United States Patent [19]
Stone

[11] Patent Number: 6,132,392
[45] Date of Patent: *Oct. 17, 2000

[54] TENSION HEADACHE RELIEVER WITH MULTIPLE PAIN RELIEVING MODALITIES

[76] Inventor: Ross G. Stone, 2601 Tecumseh Dr., West Palm Beach, Fla. 33409

[*] Notice: This patent is subject to a terminal disclaimer.

[21] Appl. No.: 08/622,987

[22] Filed: Mar. 27, 1996

Related U.S. Application Data

[63] Continuation-in-part of application No. 08/269,611, Jun. 30, 1994, Pat. No. 5,569,166, which is a continuation of application No. 07/800,164, Nov. 27, 1991, abandoned.

[51] Int. Cl.$^7$ .................................................... A61H 11/02
[52] U.S. Cl. ................................ 601/21; 601/18; 601/39; 601/51; 601/84; 601/98; 601/103; 607/3; 607/115
[58] Field of Search ..................................... 607/1–3, 115, 607/139, 140, 149, 96, 99; 601/1, 15, 18–21, 39, 46, 50–53, 84, 89, 97, 98, 103

[56] References Cited

U.S. PATENT DOCUMENTS

| | | |
|---|---|---|
| 502,776 | 8/1893 | Se Cheverell . |
| 729,317 | 5/1903 | Fleetwood . |
| 768,721 | 8/1904 | Bassell . |
| 861,849 | 7/1907 | Herndon . |
| 999,945 | 8/1911 | Aub . |
| 1,099,062 | 6/1914 | Laposkey . |
| 1,679,245 | 7/1928 | Gaertner . |
| 1,789,758 | 1/1931 | Kays ...................................... 128/790 |
| 1,849,745 | 3/1932 | Hoffman ................................ 128/791 |
| 2,569,795 | 10/1951 | Avery ..................................... 128/24.2 |
| 3,323,517 | 6/1967 | Keller . |
| 3,374,784 | 3/1968 | Brent ........................................ 128/61 |
| 3,659,614 | 5/1972 | Jankelson . |
| 3,868,951 | 3/1975 | Albrecht .................................. 128/75 |
| 3,872,859 | 3/1975 | Pitzen et al. . |
| 4,022,195 | 5/1977 | Meyer et al. ............................. 601/18 |

(List continued on next page.)

FOREIGN PATENT DOCUMENTS

| | | |
|---|---|---|
| 544544A | 6/1993 | European Pat. Off. . |
| 2287921 | 5/1976 | France . |
| 29519551 | 1/1996 | Germany . |
| 2120944 | 12/1983 | United Kingdom . |
| WO8901353 | 2/1989 | WIPO . |

OTHER PUBLICATIONS

OMS Medical Supplies, Inc., 1990 Catalog, pp. 2, 19–23, and 31.
Panasonic brochure for EP 585EB Shiatsu Massage Lounger.
Laxter Health Products brochure for Kneading–Finger Massager.
The Spinalator Company brochure for Spinalator product.
The Sharper Image Store Holiday 1991 Catalog pp. 5, 6, 11, 16, 17, 20, and 27.
Palm Beach Post, Oct. 31, 1991, Health Notes, Article entitled "Electrical Impulses Used to Help Addicts."
D. Ottoson and T. Lundeberg, Pain Treatment by TENS, 1988, pp. 20–29, 48, 50, 51, 96 and 97–99.
Judith Hooper and Dick Teresi, Would the Buddah Wear A Walkman? catalog, 1990, pp. 23–31.
Medical Designs brochure for The Spectrum System, pp. 1–24.
Instruction Manual for the Empi EPIX LX TENS Device, 1988.
East West / Dec. 1990, The Journal of Natural Health & Living, pp. 54–58, 60 and 70.

*Primary Examiner*—Kennedy J. Schaetzle
*Attorney, Agent, or Firm*—Ostrolenk, Faber, Gerb & Soffen, LLP

[57] ABSTRACT

A pain relieving device for selectively applying three or more pain relieving modalities to an upper body region of a person. The modalities include acupressure and at least two other modalities selected from the group of vibration, massage, heat, traction and electric stimulation. The device further includes a controller for enabling an operator of the pain relieving device to select which two or more of the pain relieving modalities are applied to the person at any given time. The controller causes the pain relieving apparatus to automatically apply the selected modalities to the person.

83 Claims, 13 Drawing Sheets

U.S. PATENT DOCUMENTS

| | | | |
|---|---|---|---|
| 4,117,846 | 10/1978 | Williams . | |
| 4,173,217 | 11/1979 | Johnston | 128/24.5 |
| 4,230,098 | 10/1980 | Uematsu | 128/52 |
| 4,267,838 | 5/1981 | McCall . | |
| 4,327,713 | 5/1982 | Okazaki et al. | 128/52 |
| 4,354,509 | 10/1982 | Strahwald et al. | 128/639 |
| 4,364,378 | 12/1982 | Seuss et al. | 128/24.5 |
| 4,549,536 | 10/1985 | Varjabedian . | |
| 4,580,572 | 4/1986 | Granek et al. | 128/639 |
| 4,583,547 | 4/1986 | Granek et al. | 128/639 |
| 5,086,788 | 2/1992 | Castel et al. . | |
| 5,569,166 | 10/1996 | Stone | 601/21 |

TENSION HEADACHE RELIEVER WITH MULTIPLE PAIN RELIEVING MODALITIES

CROSS-REFERENCE TO RELATED APPLICATIONS

This is a CIP application of U.S. patent application Ser. No. 08/269,611 filed Jun. 30, 1994, now U.S. Pat. No. 5,569,166, which is a continuing application of application Ser. No. 07/800,164 filed Nov. 27, 1991, now abandoned.

BACKGROUND OF THE INVENTION

1. Field of the Invention

The present invention relates to a tension headache reliever, and more particularly to a tension headache reliever that does not require the use of pharmaceuticals.

2. Description of the Prior Art

Headaches are attributable to many factors. Tension, stress, concerns about business or family problems, all cause headaches. Eye strain, sinuses, colds and flu can also cause headaches as well as overexposure to the sun, excessive consumption of alcohol, loud noises and high air or water pressure. Headaches can occur for several hours or last for many days, e.g. migraine headaches.

Presently, there are various pharmaceutical headache and pain relievers available to the public that have met with varying degrees of success in curing headaches. However, the pharmaceutical products are deficient for a number of reasons. Many of the pharmaceutical products are not effective in relieving certain types of headaches. They do not relieve the same type of headaches in different people. People often build up an immunity to these pharmaceutical products rendering them ineffective. Other people are allergic to these pharmaceutical products or cannot or do not want to ingest the chemicals in these pharmaceutical products. Also, the pharmaceutical products are aimed at curing generalized pain only, and cannot cure particular areas of pain.

Alternative methods have been developed to relieve headaches without the use of pharmaceutical products. One of these methods includes electric stimulation, i.e., applying pulses of electric energy at low current levels to the parts of the body that emanate pain.

Most electric stimulators have carbon rubber electrodes which are reusable and can be fixed to the skin with adhesive tape and are adaptable to the contour of the body region to be stimulated. The prior art recommends placement of electrodes over the occipital nerves with an intensity of stimulation high enough to produce paresthesia from occiput to vertex. If this is not successful, electrodes are placed over the forehead or temples.

To apply an electric stimulus the prior art teaches the use of TENS (Transcutaneous Electrical Nerve Stimulation) devices. TENS devices deliver electric bursts through the skin to cutaneous (surface) and afferent (deep) nerves to control pain. The use of a TENS device is an advancement in the art because of how it operates; it is able to stimulate a specific nerve to ease a specific point of pain.

There are two major theories explaining how electric stimulation relieves pain. According to the "gate control theory," pain and non-pain impulses are sent to the brain from the local nervous system. These pulses travel through the cutaneous nerves to the deeper afferent nerves and then to the spinal cord and brain. Along the path are many areas referred to as "gates." The gates control which impulses are allowed to continue to the brain. These gates prevent the brain from receiving too much information too quickly. Since the same nerve cannot carry a pain impulse and a non-pain impulse simultaneously, the stronger, non-pain impulse (from the TENS device) "controls the gate."

According to the second theory, TENS stimulation encourages the body to produce natural pain killers called endorphins. These chemicals interact with receptors, blocking the perception of pain, much as the pharmaceutical drug morphine does, but without the side effects associated with morphine.

Most TENS units can vary stimulus intensity, pulse rate, and pulse width. TENS devices can be powered by a single 9-volt battery. Modern TENS devices offer a dual or multichannel system for use with four or more electrodes. These units permit the simultaneous treatment of many points within a painful area which is particularly useful if that area is wide or the pain is radiating. These units also provide a variety of possible electrode arrangements which may be useful in treating certain pain.

The prior art also teaches devices utilizing, in addition to electric stimulus, acupressure, massage and vibration therapies to relieve pain. Acupressure involves applying physical pressure against specific parts of the body to achieve some degree of treatment or pain relief. However, these devices are complicated to operate and require an attending therapist during treatment. Further, none of the prior art devices combine the salient features of each of these approaches to relieve pain, nor do they enable such approaches to be administered simultaneously.

SUMMARY OF THE INVENTION

Accordingly, it is an object of the present invention to provide a tension headache reliever to relieve headache pain without using pharmaceuticals.

Another object is to provide such a tension headache reliever that applies different approaches, simultaneously, to relieve the same condition, i.e. combination therapy.

A further object is to provide such a tension headache reliever to relieve headache pain by using a combination of electric stimulation, acupressure, heat, vibration, traction and massage therapy.

It is also an object to provide such a tension headache reliever that provides spinal cord stimulation.

It is another object to provide such a tension headache reliever that applies combination therapy without the need for an attending therapist.

It is a further object to provide such a tension headache reliever that stimulates specific parts of the body to ease specific points of pain.

It is still a further object to provide such a tension headache reliever that is easy to operate, manufacture and repair.

It has been found that the above and other objects of the present invention are attained in a tension headache reliever including a plurality of sources of pain relieving modalities selected from the group consisting of massage, heat, vibration, acupressure, traction and electric stimulation; and means for applying at least three of the modalities, simultaneously, to a selected point at the upper body region of a person.

BRIEF DESCRIPTION OF THE DRAWINGS

For the purpose of illustrating the invention, there is shown in the drawings an embodiment which is presently preferred; it being understood, however, that the invention is not limited to the precise arrangements and instrumentalities shown.

DESCRIPTION OF THE PREFERRED EMBODIMENT

Figure 1:
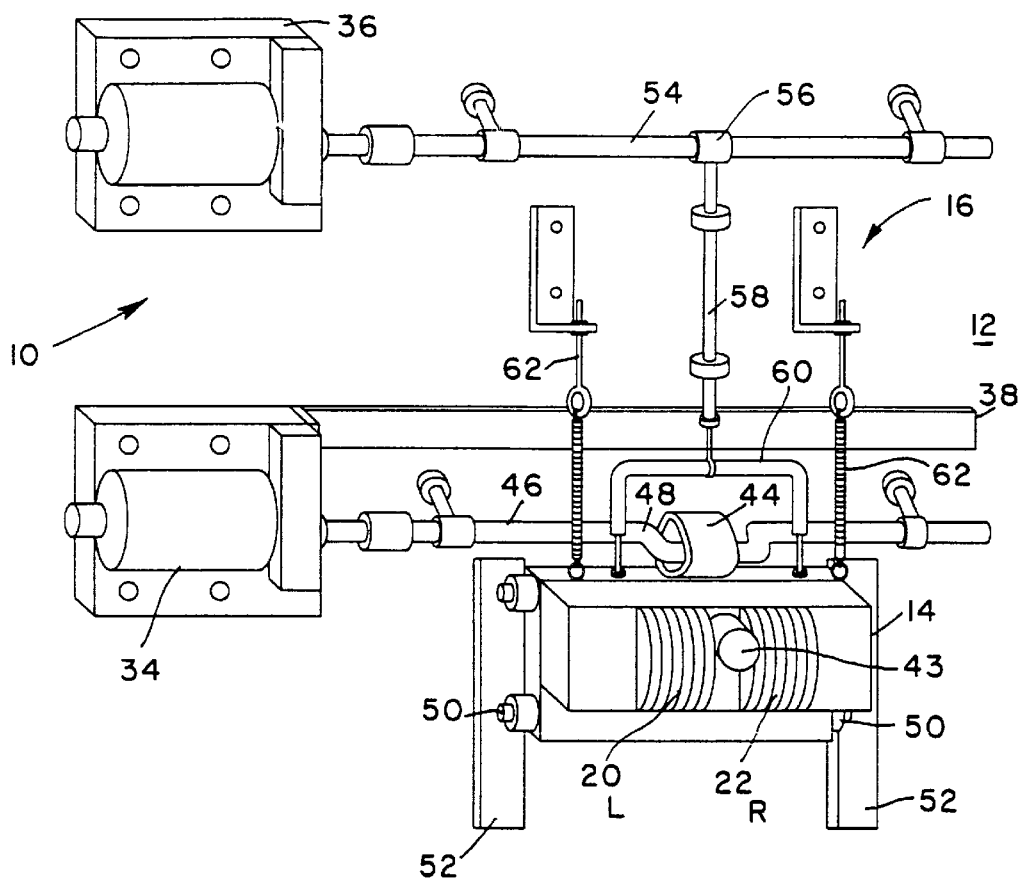
FIG. 1 is a top plan view of the tension headache reliever of the present invention.

Referring now to the drawings wherein like numerals indicate like elements, there is shown in FIG. 1 a tension headache reliever 10. The tension headache reliever 10 functions as an applied modality in physical therapy or a physician's office with a patient lying supine on a treatment table, not shown. It provides up to six modes of stimulation to relieve headache pain. The six modes of stimulation are massage, vibration, acupressure, heat, traction and electric stimulation.

Figure 3:
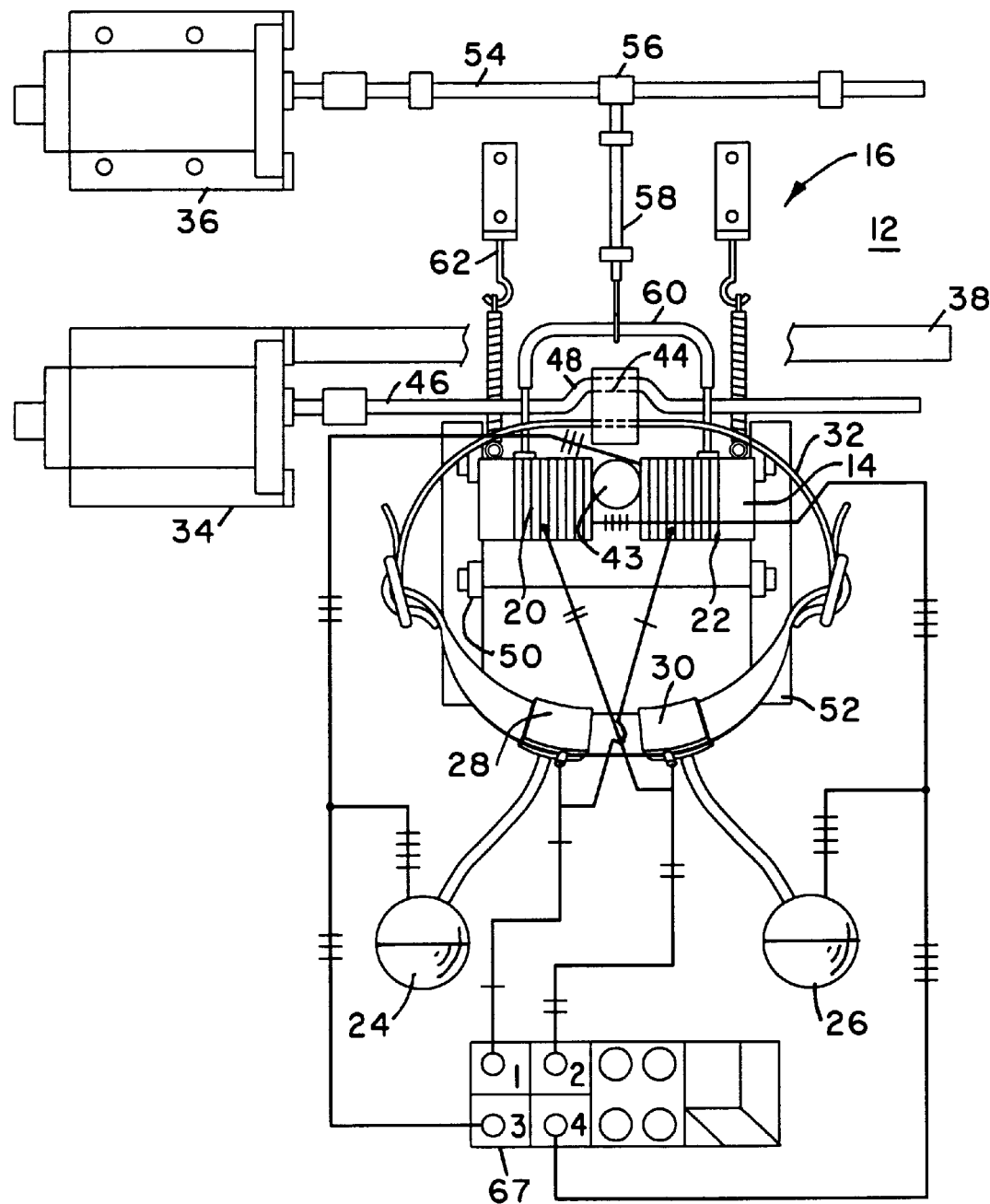
FIG. 3 is the tension headache reliever of FIG. 1 wired to a four channel electric stimulation applying device.

Referring now to FIGS. 1, 3, the tension headache reliever 10 includes a base portion 12, a mobile carriage unit 14, and a massage apparatus 16 mounted thereon to provide the acupressure, massage and vibration modes of stimulation. To provide the electric mode of stimulation, the tension headache reliever 10 includes a left coil occipital electrode 20 and a right coil occipital electrode 22 mounted on the mobile carriage unit 14, a left dome shoulder electrode 24 and a right dome shoulder electrode 26, and a left frontal electrode 28 and a right frontal electrode 30 mounted on a forehead electrode strap 32. Preferably, the heat stimulation is provided by the occipital electrodes 20, 22 and the shoulder electrodes 24, 26, although it can also be provided by the frontal electrodes 28, 30. As will be explained more fully below, the occipital electrodes 20, 22 allow any combination of the aforementioned modalities, namely, massage, vibration, acupressure, heat, traction and electric stimulation to be administered simultaneously.

The left occipital electrode 20 and the right occipital electrode 22 are in the form of semicircular coils. It is recommended that each electrode be approximately one and five-eighths inches wide, and be made up of approximately ten one-eighth inch copper wires. The left occipital electrode 20 and the right occipital electrode 22 are to be spaced approximately three-quarters of an inch apart. The electrodes can also be made of any of the known materials and by any of the known methods, e.g. molded carbon rubber, just so long as the electrodes are of a similar size and configuration to the electrodes 20, 22.

Figure 14:
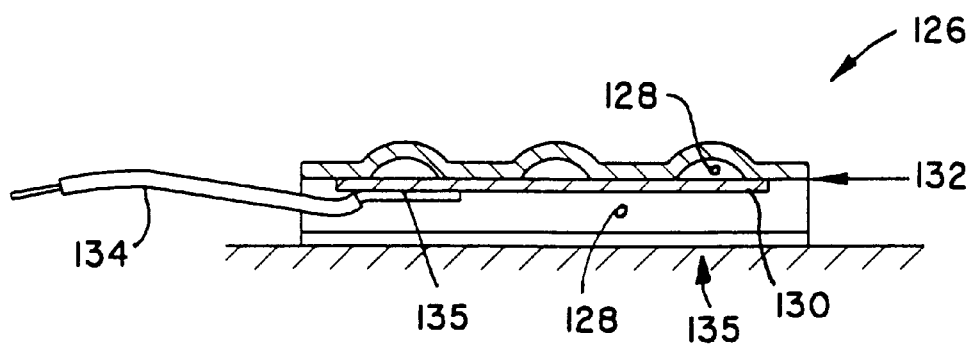
FIG. 14 is a cross-sectional view of an electrode preferred embodiment.

In a preferred embodiment, the occipital electrodes 20, 22, the shoulder electrodes 24, 26 and the frontal electrodes 30, 32 can be of the silver silicone type, FIG. 14, available from the Jupiter Instrument Company, Jupiter Fla. FIG. 14 shows a silver-silicone electrode 126. The silver-silicone electrode 126 can be molded in any shape, and the surface can be molded in any configuration to enhance contact with the patient's skin, for example FIG. 8.

The silver-silicone electrode 126 includes a molded non-conductive silicone rubber layer 128, and a conductive copper mesh layer 130 in contact with a molded conductive silicone coated-glass bead layer 132. The glass bead layer 132 is a mixture of 70–75% by weight of silver coated glass microspheres (equivalent to Potters Industries Conduct-O-Fil S3000-S Silvered Spheres) and silicone rubber. This gives the silver coated-glass bead layer 132 its conductivity and makes that layer soft and resilient.

An external electrical connection is made to the silver-silicone electrode 126 by attaching a conductive electrode wire 134 to the copper layer 130 at an attachment point 135 by soldering or by any of the known methods. The wire 134 transmits electrical stimulation, e.g., by means of a TENS, MENS or SEA device discussed below, and/or heat stimulation by means of an electric heating device, discussed below.

The silver-silicone electrode 126 is attached to an electrode support 135, e.g., the electrode strap 32, by an adhesive, or by any of the known methods such as a VELCRO brand hook and loop fastener.

Figure 5:
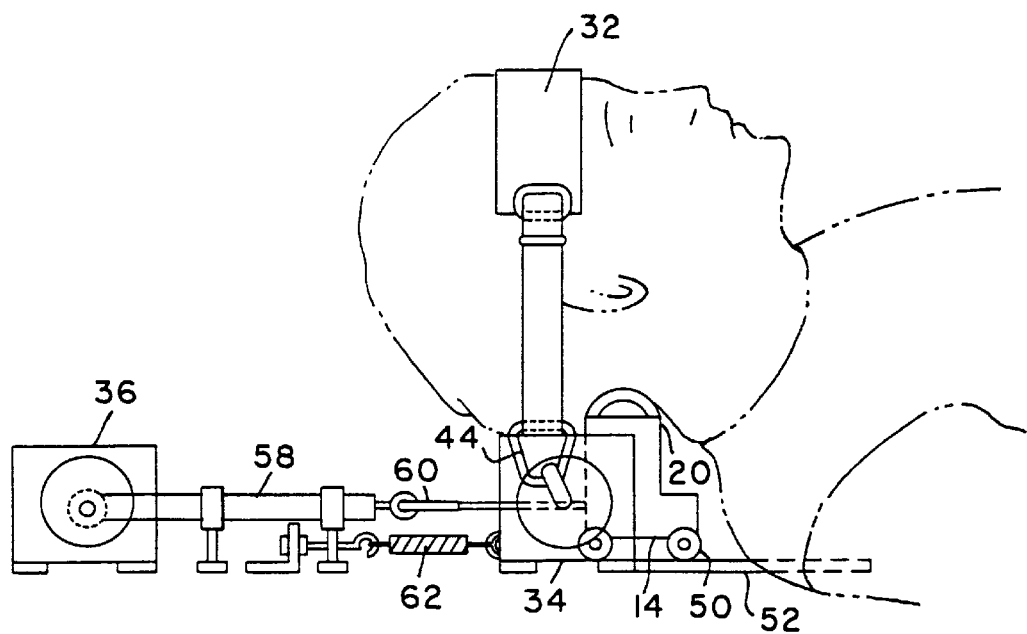
FIG. 5 is a side elevational view of the tension headache reliever of FIG. 1 in use by a patient in the supine position.

The massage apparatus 16 is powered by two electric motors 34 and 36 which receive power from a 12 volt battery, not shown. Each motor 34, 36 controls a different massage motion. The motor 34 provides a rocking motion to a patients head along an arcuate path generally perpendicular to the patient's spine, as the patient lies in a supine position on the tension headache reliever 10 as shown in FIG. 5. The motor 36 provides a back and forth or low frequency vibration motion to the patient's head along a path generally parallel to the patient's spine.

In the supine position, as shown in FIG. 5, the head is made to rest against a spring-biased head return bar 38 (FIG. 3), the occipital electrodes 20, 22 which are positioned suboccipital fossa bilaterally or below the occipital condyles of the patient's head shown at points 40 and 42 of FIG. 2 (the suboccipital region), and a centering inion placement post 43 which is positioned below the inion, not shown, and between the occipital condyles 40, 42 of the patient's head. The patient's body weight against the occipital electrodes 20, 22 and the inion post 43 generates acupressure. The inion post 43 is spring-biased to comfort the patient's head. The head return bar 38 can be padded for added comfort.

To achieve the rocking motion massage and traction, the forehead electrode strap 32 is first placed around the patient's forehead when lying in the supine position, as shown in FIG. 5. The forehead electrode strap 32 should be adjustable to fit a variety of head sizes.

The motor 34 causes the forehead electrode strap 32 to rock the patient's head using the occipital electrodes 20, 22 as a fulcrum. This rocking motion over the occipital electrodes 20, 22 provides traction to, and massages, the suboccipital region of the patient's head to reproduce a normal cervical lordotic curve. The movement of the forehead electrode strap 32 also serves to massage the frontalis muscle over the forehead.

An attachment piece 44 connects the forehead electrode strap 32 to a rotating shaft 46 which is coupled to, and driven by, the motor 34. The rotating shaft 46 includes a crank or U-shaped portion 48 which attaches the attachment piece 44 to the rotating shaft 46. When the motor 34 is turned on, it drives the rotating shaft 46 so that the U-shaped portion 48 rotates between an upper position and a lower position. When the U-shaped portion 48 is in the lower position, it causes the forehead electrode strap 32 to pull the patient's head backwards, momentarily urging the spring element of the head return bar 38 into compression. When the U-shaped portion rotates into the upper position, it releases the forehead electrode strap 32. The head return bar 38, no longer in compression, then urges the patient's head forward to return to its normal supine position to complete one cycle. This cycle is repeated continuously until relief is achieved. It is recommended that the frequency of the cycle be between 0–100 cycles per minute. A controller, e.g., control 210 of controller 198 in FIG. 16, can be used by the patient to vary the speed of the motor 34 to achieve the desired frequency.

To achieve the back and forth or low frequency vibration motion massage, the motor 36 imparts back and forth movement to the mobile carriage unit 14, causing the occipital electrodes 20, 22 to massage the suboccipital region of the patient's head. The back and forth motion can be provided to the patient's head when lying in the supine position, as shown in FIG. 5, simultaneously with, or independent from, the rocking motion that is provided by the motor 34.

The mobile carriage unit 14 includes wheels 50 which ride on carriage tracts 52 mounted on the base portion 12. The motor 36 imparts movement to the mobile carriage unit 14 using a piston-like arrangement. This configuration includes a rotating shaft 54 connected to, and driven by, the motor 36. The rotating shaft 54 includes an eccentric cam 56 coupled thereto which operatively engages a piston 58. The eccentric cam 56 preferably includes two or three lobes, not shown. The piston 58 is coupled to the carriage unit 14 by a U-shaped coupler 60.

When the motor 36 is turned on, the eccentric cam 56 is caused to rotate with the rotating shaft 54 until a lobe of the cam 56, not shown, engages the piston 58, which in turn pushes the carriage unit 14 away from the motor 36. The wheels 50 and the carriage tracts 52 should be so configured to allow longitudinal, but not lateral, movement. The carriage unit 14 is displaced approximately one-half centimeter. The movement of the carriage unit 14 places a spring-bias element or spring return 62 in tension.

When the rotation of the rotating shaft 54 disengages the lobe of the eccentric cam 56 from the piston 58, the piston 58 no longer pushes the mobile carriage unit 14; and, the spring return 62, no longer in tension, pulls the carriage unit 14 back to its original position to complete one cycle. The rotation of the rotating shaft 54 repeats the cycle until relief is achieved. It is recommended that the frequency of the cycle be between 0–150 cycles per minute. A controller, e.g., control 208 of controller 198 in FIG. 16, can be used by the patient to vary the speed of the motor 36 to achieve the desired frequency.

For additional therapeutic effect, the mobile carriage unit 14 can be fitted with an additional electric motor, not shown, to impart high frequency vibration motion to the carriage unit 14, and thus to the suboccipital region of the patient's head. The electric motor can be a simple vibration motor including an eccentric cam mounted on the shaft of the motor. Preferably, the motor should rotate approximately 3,000–11,000 rotations per minute (rpms), although other motors of varying rpms can be used. This provides a high frequency vibration massage to the suboccipital region of the patient's head in addition to the much lower frequency back and forth vibration massage provided by the motor 36. A controller, e.g., control 212 of controller 198 in FIG. 16, can be used by the patient to vary the speed of the motor and thus the intensity of the vibration.

The preferred embodiment of the tension headache reliever 10 uses electric stimulation and heat stimulation in combination with the above four modes of stimulation, namely massage, acupressure, traction and vibration to achieve pain relief. Preferably, a TENS device is used to provide the electric stimulation, although it will be appreciated by those skilled in the art that other devices can be employed such as a MENS (Microvolt Electrical Nerve Stimulation) device, an electro-acupuncture device or an SEA (Synaptic Electronic Activation) device. The SEA is the only electronic stimulation device that produces anesthesia. It also includes an application of frequency characterized by use of a remote control and a high low modulation. A MENS device is an improvement over a TENS device. A MENS device provides an electric pulse approximately three orders of magnitude less than a TENS device, i.e., less voltage. The MENS device tends to be more physiologic in that it mimics a bodies' electric signals.

The electric and heat stimulation is provided when the patient lies in the supine position as described above and as shown in FIG. 5. The forehead electrode strap 32 is adjusted so that the left frontal electrode 28 and the right frontal electrode 30 are placed over the frontal area of the patient's head, i.e., any area of the forehead up to the hairline.

The left occipital electrode 20 and the right occipital electrode 22 are positioned suboccipital fossa bilaterally or below the occipital condyles as shown at points 40, 42 of FIG. 2. The coil design of the occipital electrodes 20, 22 allows transmission of therapeutic modalities while avoiding the interference of hair.

Figure 2:
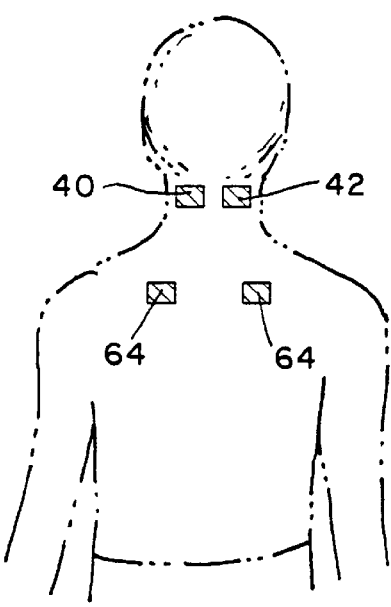
FIG. 2 illustrates the occipital and shoulder points on a patient where electric stimulation can be applied.

The left dome shoulder electrode 24 and the right dome shoulder electrode 26 are placed in contact with the patient's back, positioned at the tender points 64, 66 above the shoulder blades (superomedial portion) as shown in FIG. 2. It is recommended that the shoulder electrodes 24, 26 be dome shaped and measure approximately one and one-half inches wide and one inch high. The surface area of the shoulder electrodes 24, 26 should equal the surface area of the occipital electrodes 20, 22.

For additional therapeutic effect, the left dome shoulder electrode 24 and the right dome shoulder electrode 26 can be fitted with additional electric motors, not shown, to impart high frequency vibration motion to the electrodes. The electric motor can be a simple vibration motor including an eccentric cam mounted on the shaft of the motor. Preferably, the motor should rotate approximately 3,000–11,000 rotations per minute (rpms), although other motors of varying rpms can be used. This provides a high frequency vibration massage to the area of the patients's body around the tender points 64, 66 above the shoulder blades (superomedial portion) as shown in FIG. 2. A controller, e.g., control 214 of controller 198 in FIG. 15, can be used by the patient to vary the speed of the motor and thus the intensity of the vibration.

The placement and configuration of the forehead electrodes 28, 30, the occipital electrodes 20, 22 and the shoulder electrodes 24, 26 avoid the need for any gels to be applied between the electrodes and the area of the patient's body to be stimulated. This is because they are sufficiently pressed against the patient's body to induce electric contact. The forehead electrode strap 32 presses the forehead electrodes 28, 30 against the patient's frontal area, and the weight of the patient's body presses the occipital electrodes 20, 22 and the shoulder electrodes 24, 26 against the patient's suboccipital and shoulder areas, respectively, when the patient is in the supine position.

It should be noted that the placement of the left and right frontal electrodes 28, 30, the left and right occipital electrodes 20, 22 and the left and right dome shoulder electrodes 24, 26 is not to be specifically limited as described above. For example, while the left and right occipital electrodes 20, 22 are recommended to be positioned below the occipital condyles, the occipital condyles are bone landmarks only. Electrode placement necessarily includes all of the nerves and muscles emanating and traversing the area and the acupressure meridians thereto.

In the preferred embodiment of the invention, the electrodes 20–30 of the tension headache reliever 10 are wired to a four channel TENS device 67, as shown in FIG. 3, by using a bipolar plug or by any of the known methods. The wiring for the electrodes is the left frontal electrode 28 to the right occipital electrode 22 for the first channel. The right frontal electrode 30 to the left occipital electrode 20 for the second channel. The right occipital electrode 22 to the left shoulder electrode 24 for the third channel. And the left occipital electrode 20 to the right shoulder electrode 26 for the fourth channel.

To provide the heat stimulation, the electrodes 20, 22 and 24, 26 are wired to a conventional electric heater. Preferably, a 220 V AC electric heater including an AC to DC rectifier is used. The electric heater should be capable of delivering heat to the patient, for example through electrodes of the type shown in FIG. 14, up to a maximum of 106° F. Preferably, the heat going to the occipital electrodes 20, 22 and the shoulder electrodes 24, 26 should each have separate intensity controls and an on-off switch, e.g., controls 202, 204 and 206 of controller 198 in FIG. 16. The intensity controls should be capable of varying the intensity of the heat going to a patient up to approximately 106° F.

In this embodiment, pulsing current leaves the TENS device 67 through the first channel and travels through the left frontal electrode 28 and into the head region where the electrode 28 is positioned. The current then travels through the patient's head and is received by the right occipital electrode 22. The pulsing current then returns to the TENS unit to complete the circuit. For the second channel, the pulsing current leaves the TENS unit 67, travels through the right frontal electrode 30 and into the head region where the electrode is positioned. The current then travels through the patient's head and is received by left occipital electrode 20. The pulsing current then returns to the TENS unit to complete the circuit. For the third channel, the pulsing current leaves the TENS unit 67 and travels through the right occipital electrode 22 into the occipital region of the patient's head which is in contact with the electrode 22. The current then travels through the patient's head and body and is received by the left shoulder electrode 24. The pulsing current then returns to the TENS unit to complete the circuit. For the fourth channel, the pulsing current leaves the TENS unit 67 and travels through the left occipital electrode 20 into the region of the patient's head which is in contact with the electrode 20. The current then travels through the patient's head and body and is received by the right shoulder electrode 26. The pulsing current then returns to the TENS unit to complete the circuit. The polarities in any or all of the channels can be reversed which has been found to have a therapeutic effect.

As the left occipital electrode 20 and the right occipital electrode 22 are positioned below the occipital condyles as shown at points 40, 42 of FIG. 2, transcranial nerve stimulation is not provided. To provide transcranial stimulation, the head return bar 38 can be fitted with cranial electrodes of the same design as the left occipital electrode 20 and the right occipital electrode 22. The cranial electrodes can be wired to the frontal electrodes 28, 30 or can be wired to each other. Transcranial nerve stimulation can also be achieved by wiring the left frontal electrode 28 directly to the right frontal electrode 30.

The cross-wire arrangement, e.g. the right occipital electrode 22 to the left dome shoulder electrode 24 of the preferred embodiment provides beneficial therapeutic effect. Among others, it lowers the patient's skin resistance which allows for better penetration of electric current through the skin. It also provides spinal cord stimulation which will provide, among others, cranial and cervical spinal stimulation as well as relieve tension headaches.

Alternative arrangements have also been found to provide beneficial therapeutic effects. Exchanging or reversing the shoulder electrodes 24, 26, e.g., wiring the left occipital electrode 20 to the left shoulder electrode 24, rather than the right occipital electrode 22 to the left shoulder electrode 24 for the third channel, provides more direct anatomical stimulation of the trapezius and levator scapula. This straight-wire, as opposed to cross-wire, arrangement benefits patients having more muscular pathologies rather than spinal pathologies. Thus, straight-wire electric stimulation of the splenius capitis and cervical multifidus muscles will relieve spasm to benefit some patients, but will not be effective to treat an ailment having a spinal pathology such as spinal stenosis.

Four channel TENS devices allow the patient to have the most control over the intensity at each of the six active electrodes. Four channels also allow variance for different degrees of tenderness, right to left, top to bottom, and front to back.

As most commercially available TENS and MENS devices have two channels and electro-acupuncture devices have three channels, two and three channel wiring configurations can be used as alternative embodiments. Each wiring configuration treats a different area of the head and spine to relieve the pain.

Figure 6:
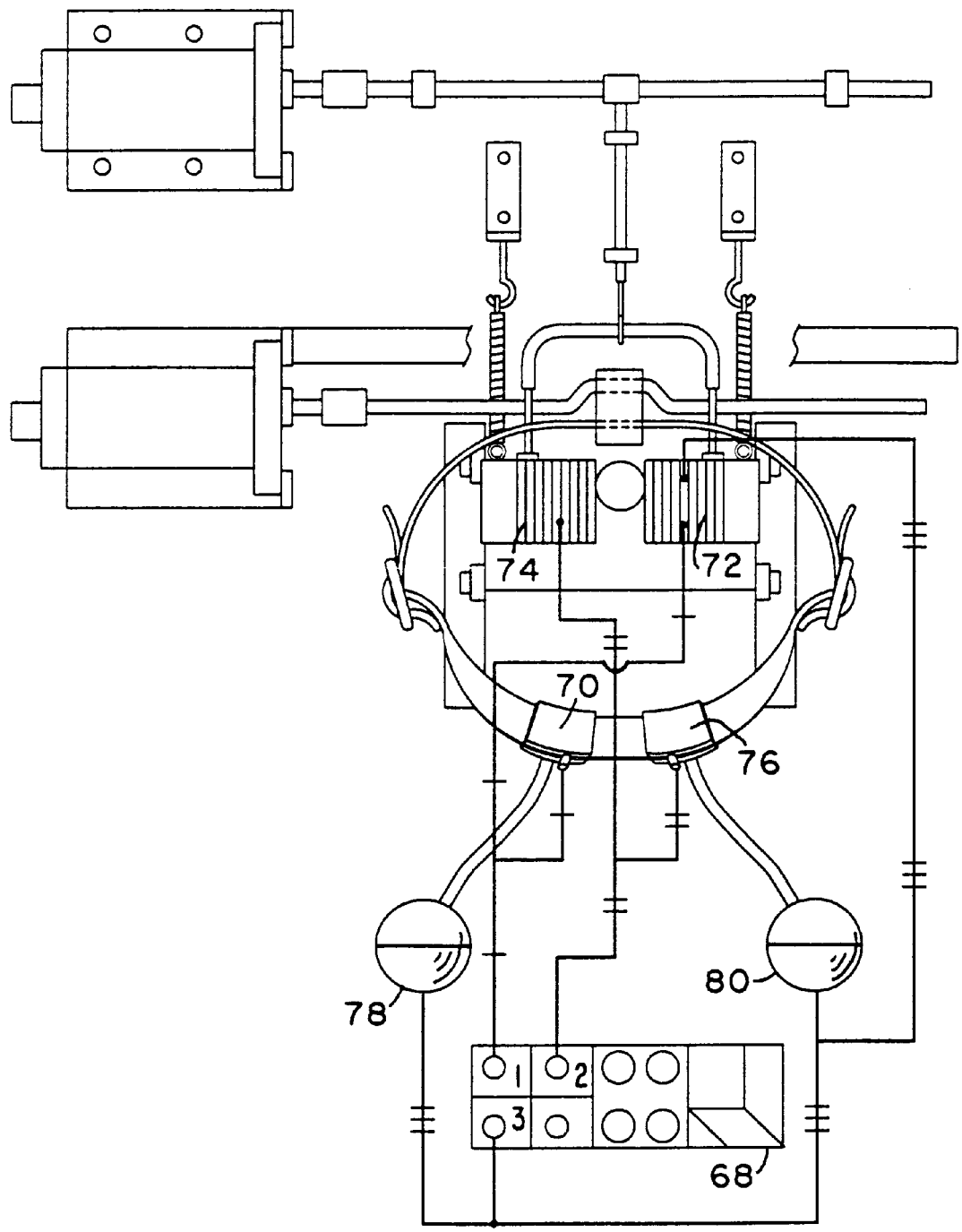
FIG. 6 is an alternative embodiment of the tension headache reliever of FIG. 1.

Referring now to FIG. 6, there is shown an alternative embodiment of the tension headache reliever 10 employing a three channel TENS device 68. The wiring is a left frontal electrode 70 to a right coil occipital electrode 72 for channel one. A left coil occipital electrode 74 to a right frontal electrode 76 for channel two. The combination of the left occipital electrode 74 and the right occipital electrode 72 to the combination of a left shoulder electrode 78 and a right shoulder electrode 80 for channel three.

Figure 7:
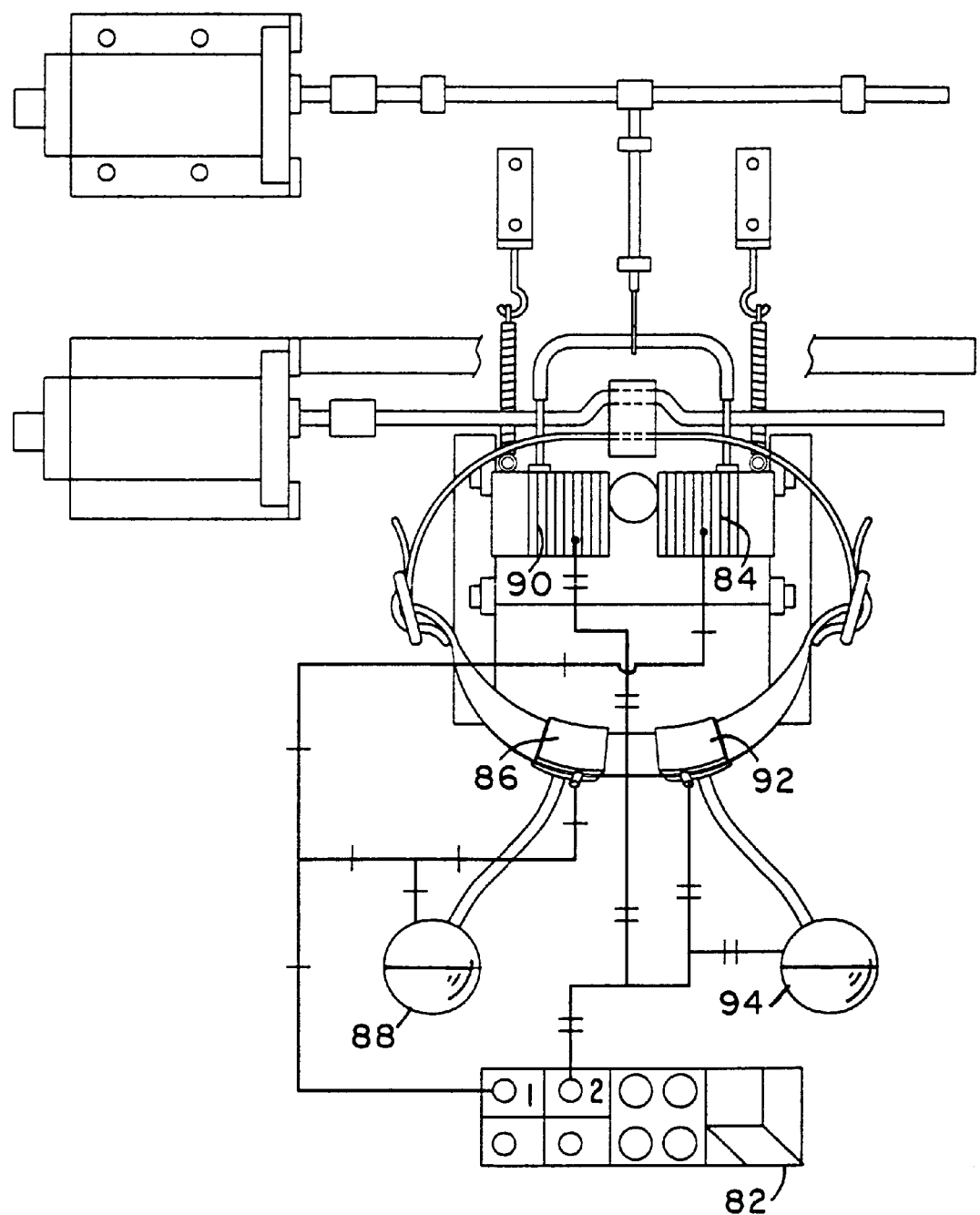
FIG. 7 is an alternative embodiment of the tension headache reliever of FIG. 1.

Referring now to FIG. 7, there is shown the alternative embodiment of the tension headache reliever 10 employing a two channel TENS device 82. The wiring is a right occipital electrode 84 to the combination of a left frontal electrode 86 and a left shoulder electrode 88 for channel one. Channel two is a left occipital electrode 90 to the combination of a right frontal electrode 92 and a right shoulder electrode 94.

The three channel wiring configuration of FIG. 6 lacks adjustability right to left between the occipital electrodes 72, 74 and the shoulder electrodes 78, 80, and lacks a crossed or interferential stimulation pattern between the occipital electrodes 72, 74 and the shoulder electrodes 78, 80. This is because in channel three, both the left occipital electrode 74 and the right occipital electrode 72 are wired to both the left shoulder electrode 78 and the right shoulder electrode 80.

The two channel wiring configuration of FIG. 7 has independent right to left stimulation, i.e., the right occipital electrode 84 is wired to both the left frontal electrode 86 and the left shoulder electrode 88, and the left occipital electrode 90 is wired to both the right frontal electrode 92 and the right shoulder electrode 94. This wiring scheme requires that the surface area of the frontal electrodes 86, 92 and the shoulder electrodes 88, 94 be decreased so that the surface area of each occipital electrode, e.g., occipital electrode 90, equals the combined surface area of the corresponding frontal and shoulder electrodes e.g., frontal electrode 92 and the shoulder electrode 94. Otherwise the electrodes will disperse the electric charge and electric stimulation will not be realized. The surface area stimulation adjustments between the frontal electrodes 86, 92 and the shoulder electrodes 88, 94 can be accomplished by covering portions of the electrode with insulation tape.

In use, the patient can operate the tension headache reliever 10 by himself without an attending therapist. The patient has control over using all or any combination of the six modes of therapy, namely, electric, acupressure, vibration, heat, traction and massage stimulation, e.g., using controller 198, FIG. 16. The patient can control the intensity of each of the modes of therapy, e.g., controls 204, 206, 208, 210, 212 and 214 of FIG. 16. It is recommended that the tension headache reliever 10 be used for approximately forty-five minutes to one hour, although for minor pain relief fifteen minutes is adequate. Of course the exact time of use will vary from patient to patient depending on the severity of the pain to be relieved, and the intensity and combination of the therapies used.

Figure 4:
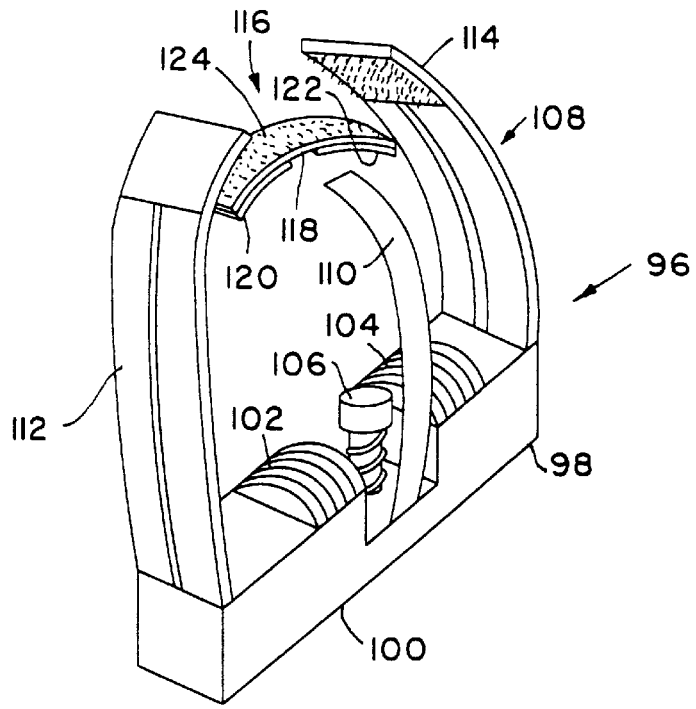
FIG. 4 is a perspective view of an alternative embodiment of the tension headache reliever of the present invention.

Referring now to FIG. 4, there is shown an alternative embodiment of the tension headache reliever 10 consisting of a transportable unit 96. The transportable unit 96 includes a base portion 98 having a surface 100 that can lay flat against a firm support such as a table, seat back or a wall. The base portion 98 includes a left coil occipital electrode 102 and a right coil occipital electrode 104 mounted thereon, separated by a centering inion placement post 106. The construction of the occipital electrodes 102, 104 and the centering inion placement post 106 are similar in construction to the occipital electrodes 20, 22 and the inion post 43 of the tension headache reliever 10 described above.

Attached to the base portion 98 is a forehead electrode strap 108 and a suspension strap 110 which extends from the base of the inion post 106. The suspension strap 110 supports the transportable unit 96 to the patient's head.

The forehead electrode strap 108 includes a first member 112 and a second member 114 extending from opposite ends of the base portion 98. The forehead electrode strap 108 also includes an electrode strip 116. The electrode strip 116 includes a substrate 118 having a left frontal electrode 120 and a right frontal electrode 122 mounted on one surface and attachment means 124 mounted on the opposite surface which is capable of being attached to the inside surface of the end portions of the first member 112 and the second member 114 of the forehead electrode strap 108.

Preferably, the electrode strip 116 is removably attached to the first member 112 and the second member 114 by a hook and loop fastener that is sold under the trademark VELCRO, although it is recognized that other means can be utilized. The attachment means 124 would then include the loop portion of the VELCRO fastener and the inside surface of the end portions of the first member 112 and the second member 114 would be the hook portion. The aforementioned construction of the forehead electrode strap 108 can also be used for the forehead electrode strap 32 of the tension headache reliever 10.

To provide vibration stimulation, the base portion 98 is fitted with a simple vibration motor, not shown, that achieves vibration by an eccentric cam, similar to the simple vibration motor fitted to the mobile carriage unit 14 of the tension headache reliever 10 discussed above.

To provide electric stimulation, the left occipital electrode 102, the right occipital electrode 104 and the left frontal electrode 120 and the right frontal electrode 122 are wired to a two channel portable TENS device that can be carried around in a person's pocket. The electrodes can be cross-wired or straight wired. Preferably, the transportable unit 96 is cross-wired so that the right frontal electrode 122 is wired to the left occipital electrode 102 for channel one, and the right occipital electrode 104 to the left frontal electrode 120 for channel two. Other wire configurations can be used, e.g., the right frontal electrode 122 to the right occipital electrode 104 for channel one, and the left occipital electrode 102 to the left frontal electrode 120. In use, a person wears the transportable unit 96 by strapping the forehead electrode strap 108 around the person's head so that the left frontal electrode 120 and the right frontal electrode 122 contact the patient's forehead. The left occipital electrode 102 and the right occipital electrode 104 are positioned suboccipital fossa bilaterally or below the occipital condyles of the patient's head as shown at points 40, 42 of FIG. 3. The inion placement post 106 is positioned below the inion, not shown, between the occipital condyles 40, 42.

The suspension strap 110 extends over the top of the person's head and should be of a sufficient length to removably attach to the attachment means 124 of the electrode strip 116. Preferably the end portion of the suspension strap 110 includes the hook portion of the VELCRO fastener which allows it to mate with the loop portion of the VELCRO fastener of the attachment means 124. The transportable unit 96 can also be fitted with a hat attachment, not shown, to secure it to the patient's head.

The first member 112 and the second member 114 of the forehead electrode strap 108 should be of a sufficient length to receive a variety of head sizes. For larger heads, the first and second members 112, 114 are adjusted so that they are farther apart on the attachment means 124 of the electrode strap. For smaller heads, the first and second members 112, 114 are adjusted so that they are closer together.

The construction of the transportable unit 96 allows the patient to administer acupressure or mechanical massage to himself. This is accomplished by the patient first pressing the base portion 98 against a firm support such as a table, seat back or a wall, and then by rolling and rocking his or her head and by leaning back in either the upright or supine position.

FIGS. 8–16 show an alternative embodiment of the tension headache reliever of the present invention. Like the tension headache reliever 10, the alternative embodiment provides up to six modes of stimulation to relieve headache pain, namely massage, vibration, acupressure, heat, traction and electric stimulation.

Figure 8:
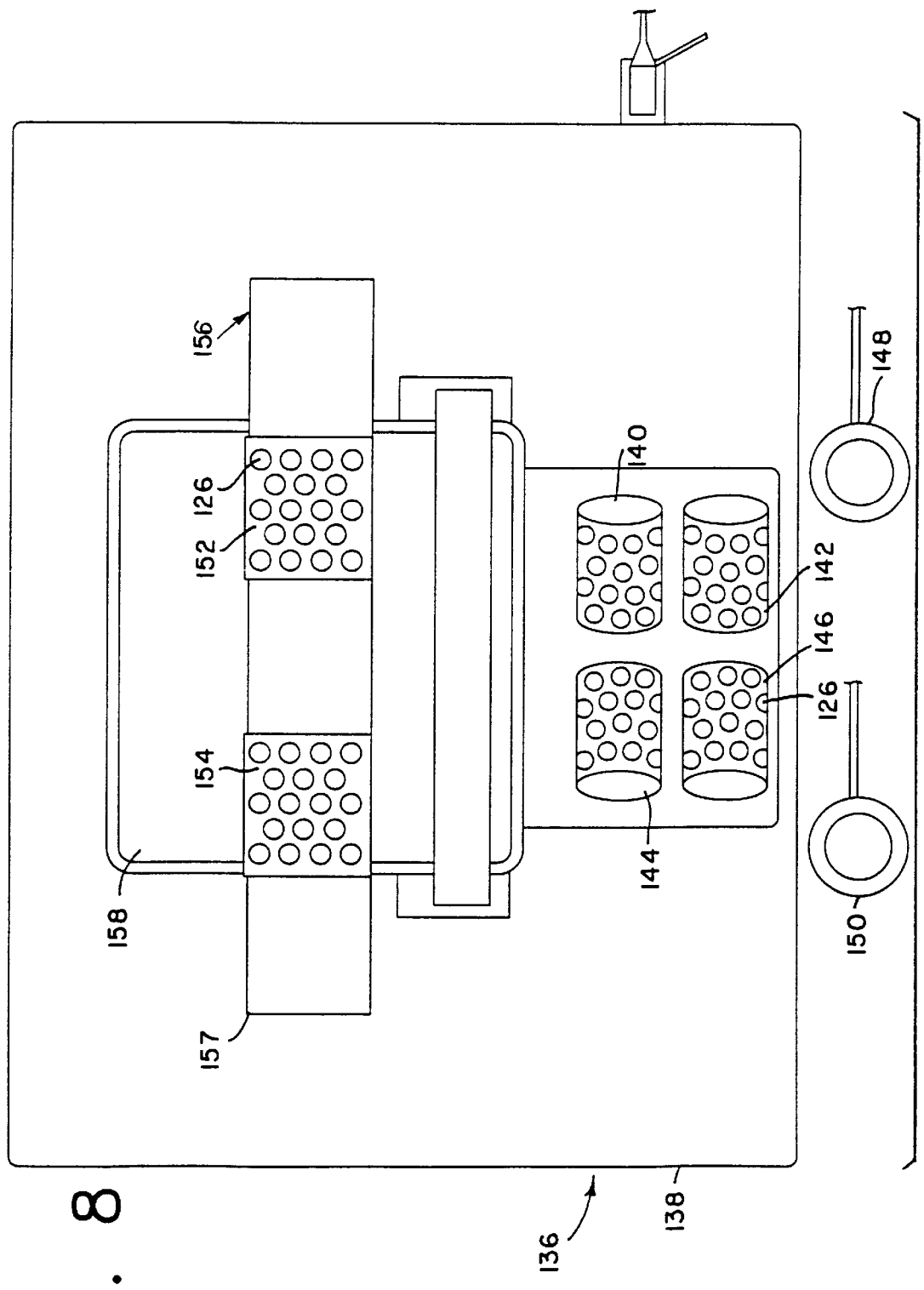
FIG. 8 is an alternative embodiment of the tension headache reliever of FIG. 1.
Figure 9:
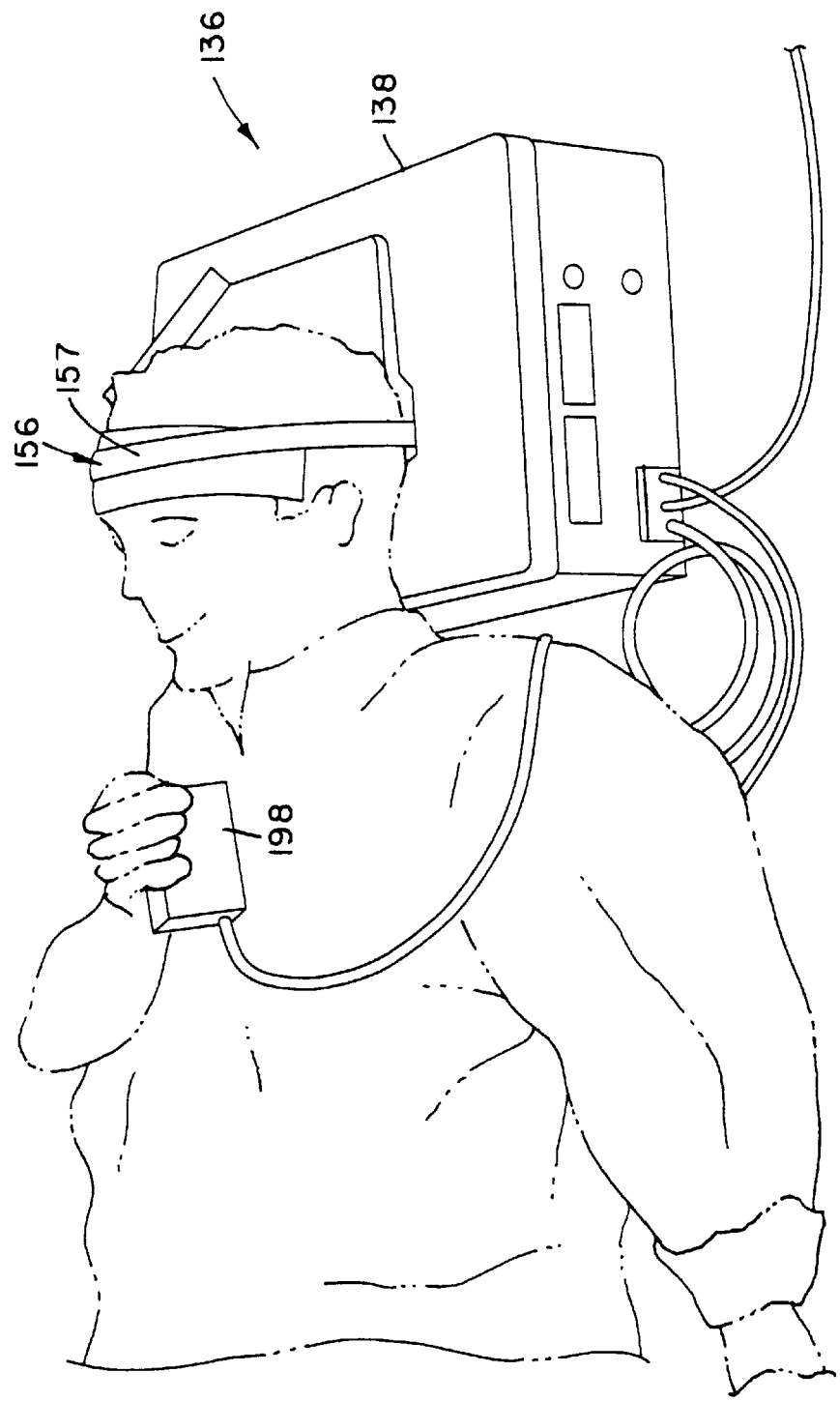
FIG. 9 is a perspective view showing the tension headache reliever of FIG. 8 in use.

Referring now to FIGS. 8 and 9 there is shown the alternative embodiment tension headache reliever 136. The tension headache reliever 136 includes a body portion 138 which houses the means for delivering the modes of stimulation to relieve headache pain.

To provide the electric and heat modes of stimulation, the tension headache reliever 136 includes a group of four occipital electrodes, an upper left occipital electrode 140, a lower left occipital electrode 142, an upper right occipital electrode 144 and a lower right occipital electrode 146, and a left shoulder electrode 148 and a right shoulder electrode 150. Like the tension headache reliever 10, the occipital electrodes 140–146 allow any combination of the massage, vibration, acupressure, heat, traction and electric stimulation modalities to be administered simultaneously.

Figure 15:
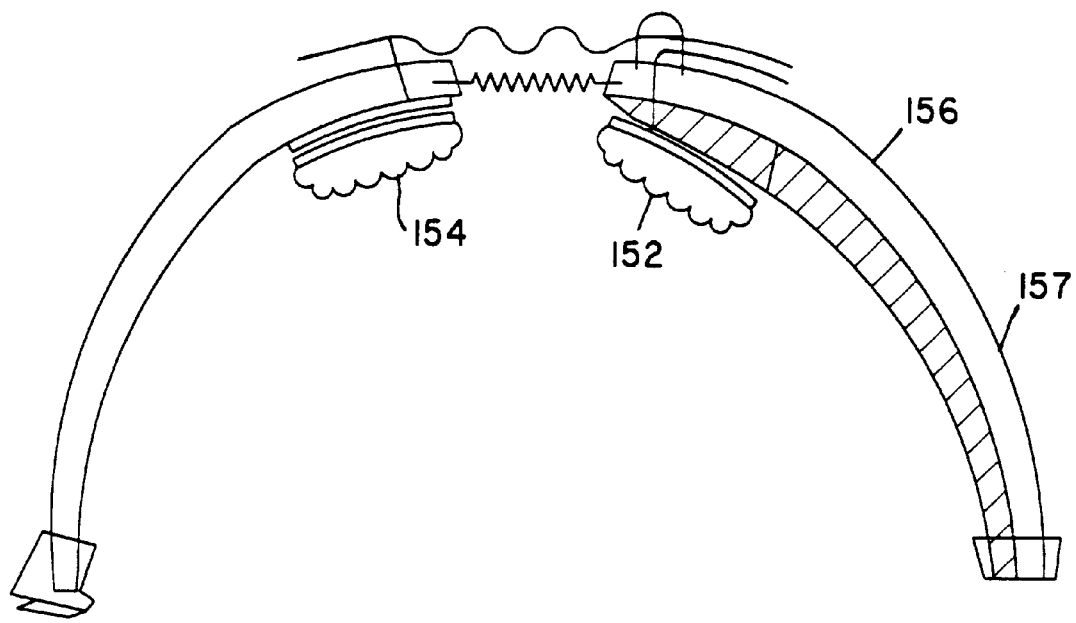
FIG. 15 is a side elevational view of the headpiece of the tension headache reliever of FIG. 8.

To further provide the electric mode of stimulation, the tension headache reliever 136 includes a left frontal electrode 152 and a right frontal electrode 154 mounted on an electrode strap or headpiece 156 by velcro or any of the known methods, e.g., stitching, glue, snaps etc., FIG. 15. The heat stimulation can also be provided by frontal electrodes 152, 154, although it is not recommended.

Preferably, the occipital electrodes 140–146, the shoulder electrodes 148, 150 and the frontal electrodes 152 and 154 are of the silver silicone type described above. The surface of the occipital electrode 140–146 and the frontal electrodes 152, 154, e.g., the silicone coated glass bead layer 132 of FIG. 14, are preferably molded to include a series of raised half spheres on its surface, as shown in FIG. 8, to allow better contact with the patient.

Referring now to FIG. 15, the occipital electrodes 140–146 are made by wrapping a silver silicone electrode, of the type shown in FIG. 14, around a molded hollow cylinder 147 by any of the known methods.

Referring now to FIG. 9, in the supine position, the patient's head is positioned on the tension headache reliever 136 so that the occipital electrodes 140–146 are positioned suboccipital fossa bilaterally or below the occipital condyles of the patient's head region. The back of the top portion of the patient's head is made to rest against a pillow portion 158 of the tension headache reliever 136. The patient's body weight against the occipital electrodes 140–146 generates acupressure.

Figure 10:
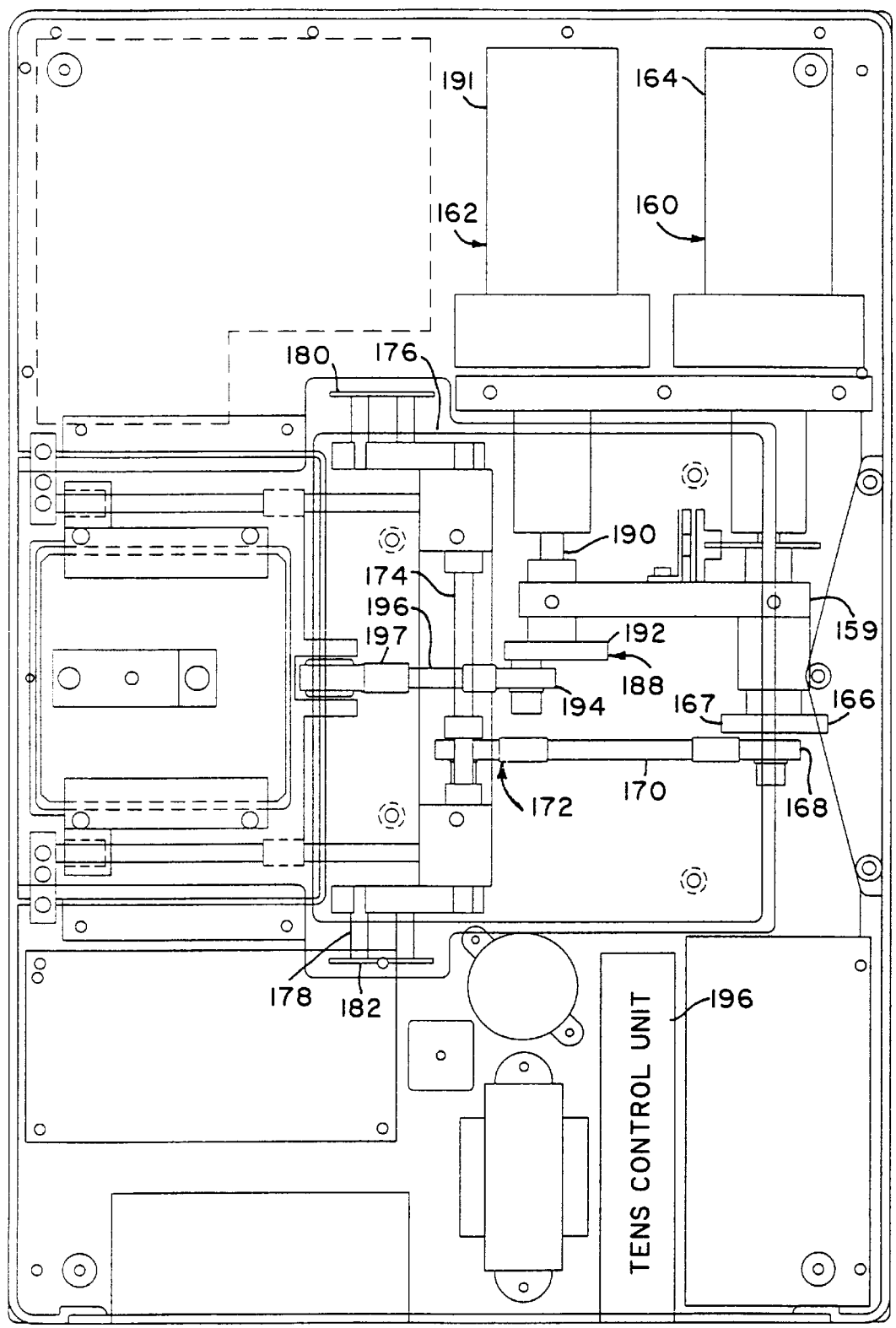
FIG. 10 is a top plan view of the interior workings of the tension headache reliever of FIG. 8.
Figure 11:
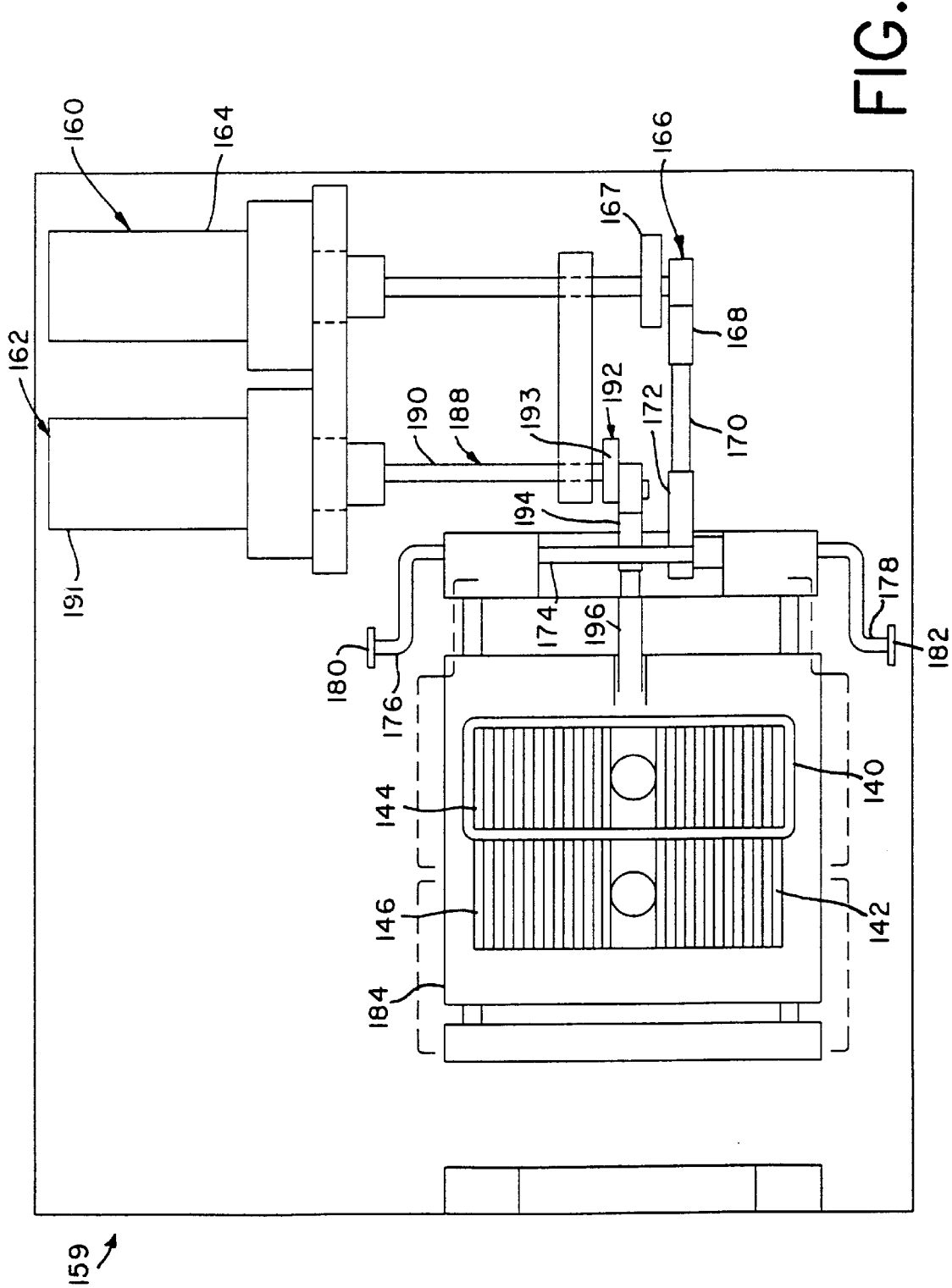
FIG. 11 is a top plan view of the massage apparatus of the tension headache reliever of FIG. 8.
Figure 12:
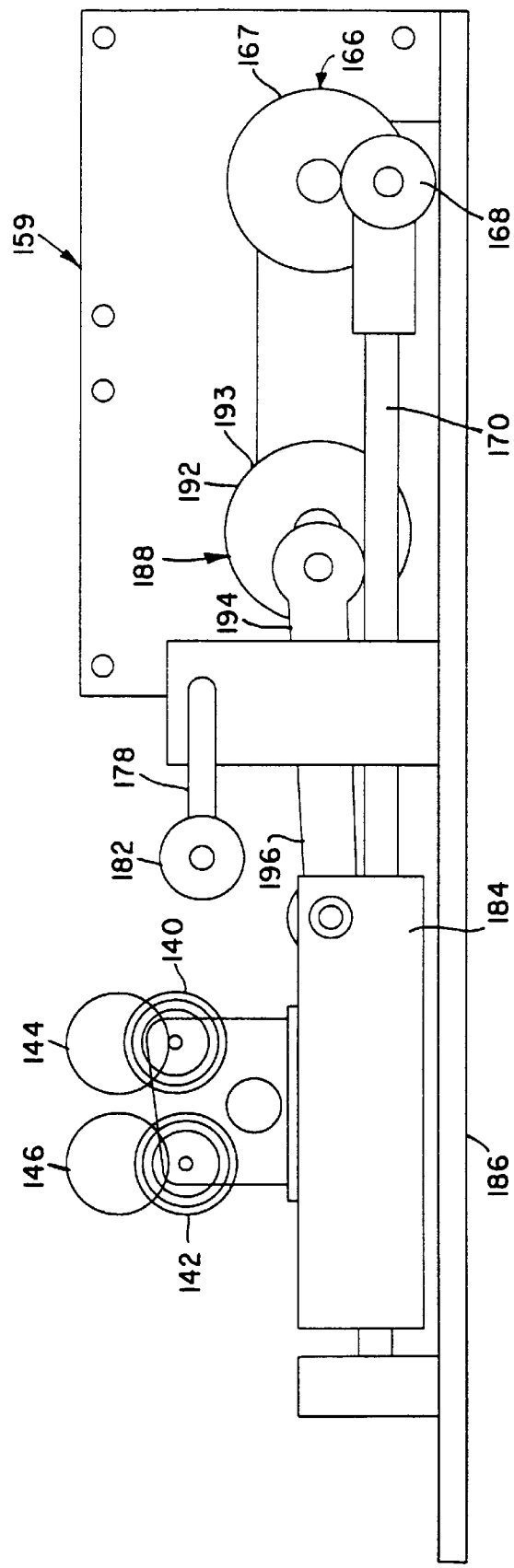
FIG. 12 is a side view of the massage apparatus of FIG. 11.
Figure 13:
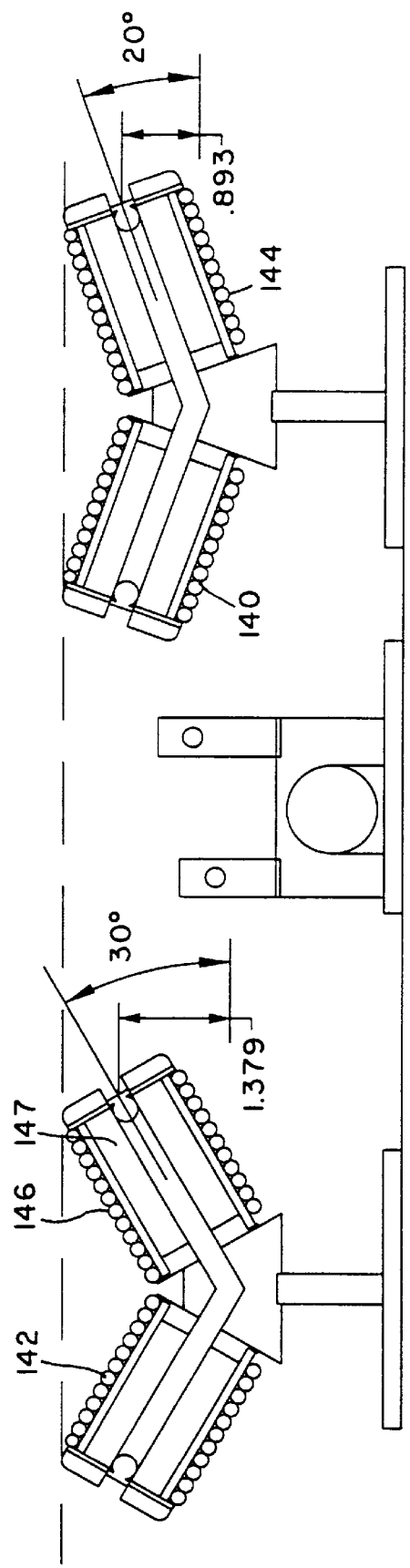
FIG. 13 is a view of the occipital electrodes of the tension headache reliever of FIG. 8.

Like the tension headache reliever 10, a massage apparatus 159 provides acupressure, massage, traction and vibration modes of stimulation. Referring now to FIGS. 10–12, the massage apparatus 159 includes a rocking assembly 160 and a back and forth assembly 162 which each provide a different massage motion. The assembly 160 provides traction and a rocking motion to a patient's head along an arcuate path generally perpendicular to the patient's spine as the patient lies in the supine position as shown in FIG. 9. The assembly 162 provides a back and forth or low frequency vibration motion to the patient's head along a path generally parallel to the patient's spine.

To achieve the rocking motion massage and traction, the head piece 156 is first placed around the patient's head when lying in the supine position as shown in FIG. 9. Preferably, the headpiece 156 is made up of an adjustable elastic strap 157 constructed by any of the known methods to adjust around the patient's head.

As explained above, the rocking assembly 160 causes the head piece 156 to rock the patient's head using the occipital electrodes 140–146 as a fulcrum. This rocking motion over the occipital electrodes 140–146 provides traction to, and massages, the suboccipital region of the patient's head to reproduce a normal cervical lordotic curve. The movement of the headpiece 156 also serves to massage the frontalis muscle over the forehead.

Preferably, the rocking assembly 160 causes the headpiece 156 to rock the patient's head using a standard crankshaft configuration, although other known methods can be used. As can be shown in FIGS. 10–12, a motor 164 drives a crank shaft 166. The crank shaft 166 includes a pulley 167 which drives a crank throw 168. The crank throw 168 is connected to a connecting rod 170 which causes the rod 170 to move in a back and forth or piston-like fashion. Similarly, the connecting rod 170 is operatively engaged to a second crank shaft 172 which drives a connecting rod 174. i.e., the piston-like movement of the connecting rod 170 causes the crank shaft 172 to rotate the connecting rod 174.

Attached to opposite ends of the connecting rod 174 are S-shaped or crank portions 176, 178. Rotation of the connecting rod 174 causes the ends 180, 182 of the crank portions 176, 178 to move in an up and down fashion.

The ends of the headpiece 156, not shown, are attached to the ends 180, 182 of the crank portions 176 and 178. Thus, when the rocking assembly 160 is activated, the crank portions 176, 178 are caused to be rotated. When the ends 180, 182 are in a lower position, this causes the forehead headpiece 156 to pull the patient's head backwards to provide traction. When the ends 180, 182 rotate to the upper position, it releases the forehead electrode elastic 156. Due to the cushiness of the pillow portion 158, the patient's head is urged to return forward to its normal supine position to complete one cycle. This cycle is repeated continuously until relief is achieved. It is recommend that the frequency of the cycle be between 0–100 cycles per minute.

To achieve the back and forth or low frequency vibration motion massage, the back and forth assembly 162 imparts back and forth movement to a carriage assembly 184 which carries the occipital electrodes 140–146. This causes the occipital electrodes to massage the suboccipital region of the patient's head. The back and forth motion can be provided to the patient's head when lying in the supine position, as shown in FIG. 9, simultaneous with, or independent from the rocking motion that is provided by the rocking assembly 160.

The carriage assembly 184 is operatively engaged to a crank shaft 188 and is slidable along a base 186 by using conventional bearings such as ball bearings or oil bearings or any other means known to those skilled in the art. The crank shaft 188 includes a connecting rod 190 driven by a motor 191. The connecting rod 190 is operatively engaged to a cam shaft 192. The cam shaft 192 includes a pulley 193 which drives a cam throw 194. The cam throw 194 is connected to a connecting rod 196. The connecting rod 196 is attached to the carriage assembly 184 by a threaded ball bearing coupling 197 or by any of the known methods.

The back and forth assembly 162 rocks the carriage assembly 184 when the motor 191 rotates the connecting rod 190 and the pulley 193. The pulley's rotation causes the crank throw 194 to drive the connecting rod 196 in a back and forth or piston-like arrangement which rocks the carriage assembly 184. The movement of the pulley 193 in a complete circular motion causes the carriage assembly 184 to move in one back and forth cycle. This cycle is repeated continuously until relief is achieved. It is recommended that the frequency of the cycle be between 0–150 cycles per minute.

Like the tension headache reliever 10, the carriage assembly 186 is preferably fitted with an additional electric motor, not shown, to impart high frequency vibration motion to the occipital electrodes 140–146, and thus to the suboccipital region of the patient's head. The electric motor can be the same as described above.

Preferably, the shoulder electrodes 148,150 are also fitted with an additional electric motor, not shown, to impart high frequency vibration motion to the patient's shoulder region in the area of the electrodes.

Like the tension headache reliever 10, a TENS, MENS, SEA or other electrical stimulation device is used to provide the electrical stimulation, although other devices in the art can be employed. As shown in FIG. 10, a TENS or other electrical stimulation device 196 can be incorporated in the body portion 138 of the tension headache reliever 136, or can be attached to the unit externally by any of the known methods.

The electric and heat stimulation to the tension headache reliever 136 is provided in a similar manner to that described above for the tension headache reliever 10. The main difference is that four occipital electrodes 140–146 are positioned suboccipital fossa bilaterally instead of two.

The tension headache reliever 136 can be attached to a four, three or two channel TENS or other electrical stimulation device, as described above for the tension headache reliever 10. The wiring for the electrodes can also be accomplished as described above. Preferably, the wiring for the electrodes is the left frontal electrode 152 to the left shoulder electrode 148, the right frontal electrode 154 to the right shoulder electrode 150, the upper left occipital electrode 142 to the lower right occipital electrode 144, and the upper right occipital electrode 146 to the lower left occipital electrode 140.

Alternatively, the wiring configuration can be the left frontal electrode 152 to the right shoulder electrode 150, the right frontal electrode 154 to the left shoulder electrode 148, the upper left occipital electrode 142 to the lower right occipital electrode 144 and the upper right occipital electrode 146 to the lower left occipital electrode 140.

Figure 16:
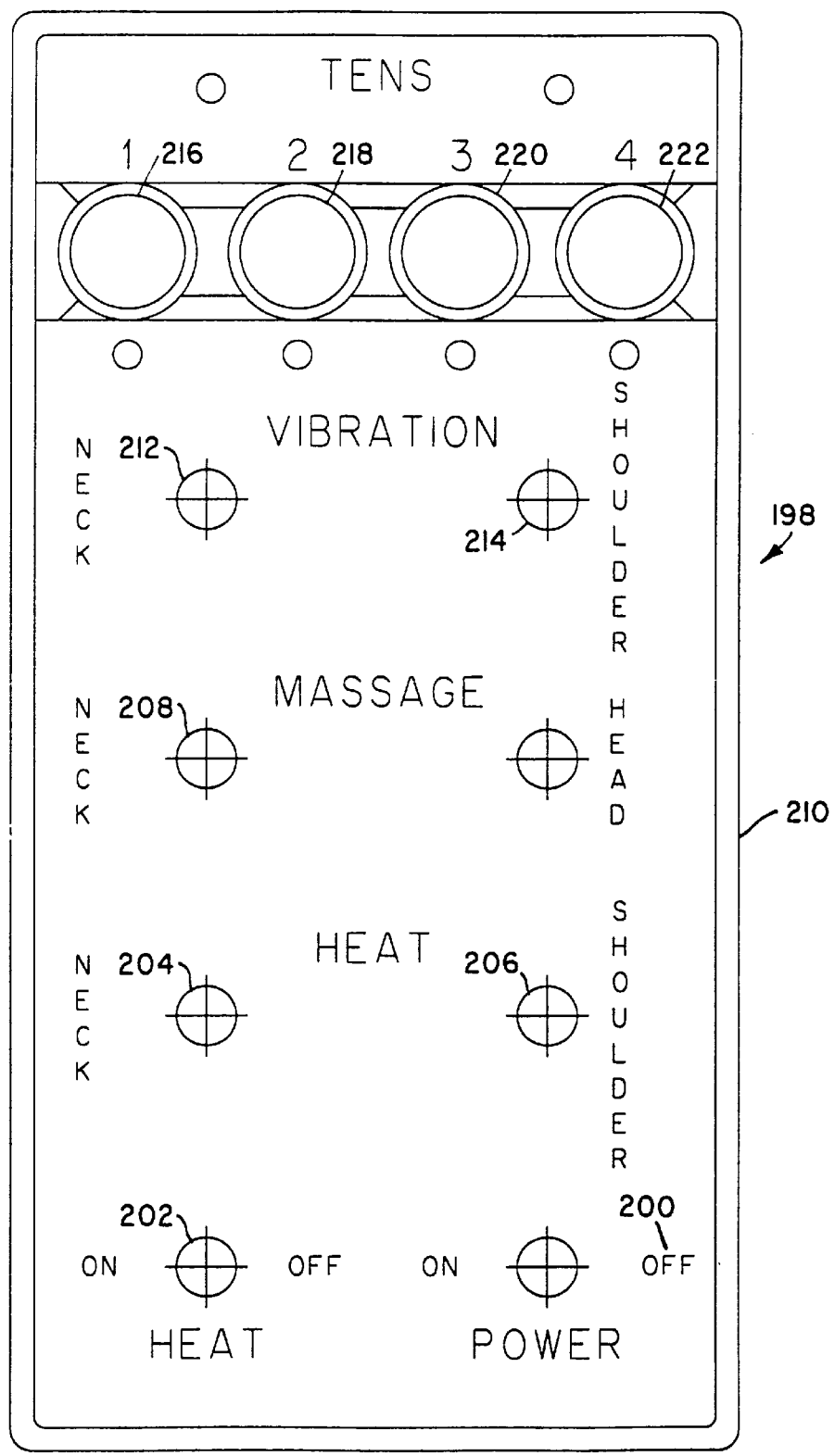
FIG. 16 is the top plan view of the hand held controller of the tension headache reliever of FIG. 8.

Referring now to FIG. 16, there is shown a hand held controller 198 that can be used with tension headache reliever 10 or 136 to select which one or more of the electric, vibration, massage, traction and heat modalities are to be applied to the patient at any one given time. The modalities can be applied individually or in any combination. The controller can also control the intensities of each of these modalities.

A control 200 controls the power to the tension headache reliever 136 or 10. A control 202 separately controls the power of the heat going to the occipital electrodes 140–146 and the shoulder electrodes 148, 150 of tension headache reliever 136, for example. A control 204 varies the intensity of the heat going to the occipital electrodes 140–146 and a control 206 varies the intensity of the heat going to the shoulder electrodes 148, 150.

Controls 208 and 210 control the intensity/speed of the massage apparatus. The control 208 controls the intensity/speed of the back and forth motion imparted to the occipital electrodes 140–146 by the back and forth assembly 162. The control 210 varies the intensity/speed of the rocking/traction motion imparted to the head by the rocking assembly 160.

A control 212 varies the intensity of the vibration motor that imparts high frequency vibration to the occipital electrodes 140–146. A control 214 controls the intensity of the vibration motor that imparts high frequency vibration to the shoulder electrodes 148 and 150.

Controls 216–222 control each of the channels of a four channel TENS device that is built into the body portion 138 of the tension headache reliever 136. If, as explained above, a separate TENS device is used, it can be separately controlled by controls that appear on the TENS unit itself, which tends to be the size of a cigarette box.

The tension headache reliever of the present invention relieves headache pain without using pharmaceuticals. It applies different approaches simultaneously to relieve the same condition, i.e. utilizes combination therapy. The tension headache reliever relieves pain by using a combination of therapies, namely electric, acupressure, vibration, heat, traction and massage stimulation. The cross-wiring arrangement provides spinal cord stimulation to additionally relieve pain having spinal pathologies. The tension headache reliever is easy to operate and can be operated without an attending therapist. It is also easy to manufacture and repair.

It should be realized that the tension headache reliever can also be utilized in combination with other methods or machines that are designed for pain relief or for relaxation in general. For instance, the tension headache reliever of the present invention can be used in combination with any one of a number of commercially available "light and sound machines" which utilize pulsating lights and sound for relaxation therapy.

Although the present invention has been described in relation to particular embodiments thereof, many other variations and modifications and other uses will become apparent to those skilled in the art.

What is claimed is:

1. A pain relieving device comprising;

pain relieving apparatus for selectively applying three or more pain relieving modalities to an upper body region of a person, the modalities including acupressure and at least two other modalities selected from the group of vibration, massage, heat, and electric stimulation;

an electrode for applying the heat and electric stimulation modalities;

means for enabling an operator of the pain relieving device to select which three or more of the pain relieving modalities are applied to the person at any given time; and means for causing the pain relieving apparatus to automatically apply the selected modalities to the person.

2. The pain reducing device of claim 1, wherein the group of modalities includes traction.

3. The pain relieving device of claim 1, wherein the electrode is a silver-silicone electrode made from a mixture of approximately 70–75% by weight silver coated glass microspheres and silicone rubber.

4. The pain relieving device of claim 1, wherein the electrode applies the vibration modality.

5. A device for relieving pain by applying pain relieving modalities comprising;

a fulcrum for supporting and contacting a person's head region at an area generally below the occipital condyles when the person is in the supine position;

means for applying electric current to the fulcrum to electrically stimulate the area generally below the occipital condyles;

a first heater to apply heat to the fulcrum to heat the area generally below the occipital condyles;

a massager for reciprocating the fulcrum to massage the area generally below the occipital condyles, and for reciprocating the person's head region on the fulcrum to massage the area generally below the occipital condyles; and a vibrator for vibrating the fulcrum to vibrate the area generally below the occipital condyles.

6. The pain relieving device of claim 5, further comprising a movable carriage, wherein the fulcrum is mounted on the moveable carriage and the massager reciprocates the carriage along a path generally parallel to the person's spine.

7. The pain relieving device of claim 5, wherein the massager reciprocates the person's head region on the fulcrum along an arcuate path generally perpendicular to the person's spine.

8. The pain relieving device of claim 7, wherein the massager includes a strap for encircling the forehead of the person to place the person's head in traction when it is reciprocated on the fulcrum.

9. The pain relieving device of claim 5, wherein the electric current applying means includes one of a TENS and MENS device.

10. The pain relieving device of claim 5, further including a second heater for applying heat to stimulate the shoulder region of a person.

11. The pain relieving device of claim 10, further including means for applying electric current to electrically stimulate the frontal region and the shoulder region of the person.

12. The pain relieving device of claim 11, wherein the electrode includes a first occipital electrode, a second occipital electrode, a third occipital electrode and a fourth occipital electrode.

13. The pain relieving device of claim 12, wherein the electric current applying means to electrically stimulate the frontal region includes a left frontal electrode and a right frontal electrode adapted to generally be in contact with the frontal region of the person's head.

14. The pain relieving device of claim 13, wherein the electric current applying means to electrically stimulate the shoulder region includes a left shoulder electrode and a right shoulder electrode adapted to be in contact with the area generally above the person's shoulder blades.

15. The pain relieving device of claim 14, wherein the shoulder electrodes are silver silicone electrodes made from a mixture of approximately 70–75% by weight silver coated glass microspheres and silicone rubber.

16. The apparatus of claim 14, wherein the left shoulder electrode and the right shoulder electrode include a vibration motor to vibrate the shoulder area of the person.

17. The pain relieving device of claim 13 further including means for applying electric current between the left frontal electrode and the left shoulder electrode, the right frontal electrode and the right shoulder electrode, the first occipital electrode and the fourth occipital electrode, and the third occipital electrode and the second occipital electrode.

18. The pain relieving device of claim 14, wherein the frontal electrodes are silver silicone electrodes made from a mixture of approximately 70–75% by weight silver coated glass microspheres and silicone rubber.

19. The pain relieving device of claim 5, wherein the electrode is a silver silicone electrode made from a mixture of approximately 70–75% by weight silver coated glass microspheres and silicone rubber.

20. The apparatus of claim 5, wherein the pain relieving device includes a controller for enabling an operator of the pain relieving device to select which three or more of the pain relieving modalities are applied to the person at any given time, the controller for causing the pain relieving apparatus to automatically apply the selected modalities to the person.

21. A pain relieving device comprising:

a movable carriage;

a first occipital electrode, a second occipital electrode, a third occipital electrode, and a fourth occipital electrode mounted on the carriage, the electrodes adapted to support a person's head when the person is lying in the supine position, and adapted to be in contact with the general area of the person's head below the occipital condyles;

a strap for encircling the forehead of the person;

a massage apparatus to reciprocate the strap so that the person's head reciprocates along an arcuate path in a direction generally perpendicular to the person's spine, and to reciprocate the carriage in a direction generally parallel to the patient's spine;

means for applying an electric current to the electrodes to provide electric stimulation; and a heater for applying heat to the electrodes to provide heat stimulation to the general area of the person's head below the occipital condyles.

22. The pain relieving device of claim 21, further including a vibrator to vibrate the general area of the person's head below the occipital condyles.

23. The pain relieving device of claim 21, wherein the strap includes a first frontal electrode and a second frontal electrode adapted to generally be in contact with the frontal region of a person's forehead.

24. The pain relieving device of claim 23 further including a first shoulder electrode and a second shoulder electrode adapted to be in contact with the region generally above the person's shoulder blades.

25. The pain relieving device of claim 24 further including means for applying the electric current between the first occipital electrode and the second frontal electrode.

26. The pain relieving device of claim 24 further including means for applying the electric current between the first occipital electrode and the second shoulder electrode.

27. The pain relieving device of claim 24 further including means for applying the electric current between the first occipital electrode and the second frontal and the second shoulder electrodes.

28. The pain relieving device of claim 24 further including means for applying electric current between the first and second occipital electrodes and the first and second shoulder electrodes.

29. The pain relieving device of claim 24, wherein the first shoulder electrode and the second shoulder electrode include vibrators to vibrate the region generally above the person's shoulder blades.

30. The pain relieving device of claim 24, wherein the heater is adapted and arranged so that the first shoulder electrode and the second shoulder electrode apply heat stimulation to the region generally above the person's shoulder blades.

31. The pain relieving device of claim 24, further including means for applying the electric current between the first frontal electrode and the first shoulder electrode, the second frontal electrode and the second shoulder electrode, the first occipital electrode and the fourth occipital electrode, and the third occipital electrode and the second occipital electrode.

32. The pain relieving device of claim 24, further including means for applying the electric current between the first frontal electrode and the second shoulder electrode, the second frontal electrode and the first shoulder electrode, the first occipital electrode and the fourth occipital electrode, and the third occipital electrode and the second occipital electrode.

33. The pain relieving device of claim 24, further including means for applying heat stimulation to the occipital electrodes and the shoulder electrodes.

34. The pain relieving device of claim 21 further including means for applying the electric current between the general areas of the person's upper body selected from the group consisting of the area below the occipital condyles, the frontal region and the area above the shoulder blades to provide electric stimulation.

35. The pain relieving device of claim 21, wherein the massage apparatus includes a motor operatively engaged to the strap and a crank means driven by the motor.

36. The pain relieving device of claim 21, wherein the person's head is in traction when the strap encircles the forehead of the person and the head is reciprocated along an arcuate path in a direction generally perpendicular to the person's spine.

37. The pain relieving device of claim 21, wherein the massage apparatus for reciprocating the carriage includes a motor, a rotatable shaft driven by the motor, and a crankshaft assembly mounted on the rotatable shaft.

38. A pain relieving device comprising;
pain relieving apparatus for selectively applying three or more pain relieving modalities to an upper body region of a person, the modalities including acupressure and at least two other modalities selected from the group of vibration, massage, heat, and electric stimulation;
an electrode for applying the heat and electric stimulation modalities; and
a controller in operative engagement with the modalities for enabling an operator of the pain relieving device to select which two or more of the pain relieving modalities from the group are applied to the person at any given time, the controller causing the pain relieving apparatus to automatically apply the selected modalities to the person.

39. The pain relieving device of claim 38, wherein the electrode is a silver-silicone electrode made from a mixture of approximately 70–75% by weight silver coated glass microspheres and silicone rubber.

40. The pain relieving device of claim 38, wherein the electrode applies the vibration modality.

41. A pain relieving device comprising;
pain relieving apparatus for selectively applying three or more pain relieving modalities to an upper body region of a person, the modalities including acupressure and at least two other modalities selected from the group of vibration, heat, massage, and electric stimulation;
an electrode for applying the heat and electric stimulation modalities; and
a controller in operative engagement with the modalities for enabling an operator of the pain relieving device to select which one or more of the pain relieving modalities from the group are applied to the person at any given time, the controller causing the pain relieving apparatus to automatically apply the selected modalities to the person.

42. The pain relieving device of claim 41, wherein the electrode is a silver-silicone electrode made from a mixture of approximately 70–75% by weight silver coated glass microspheres and silicone rubber.

43. The pain relieving device of claim 41, wherein the electrode applies the vibration modality.

44. A pain relieving device comprising;
apparatus for selectively applying three or more pain relieving modalities to an upper body region of a person, the modalities including acupressure and at least two other modalities selected from the group of vibration, heat, massage, and electric stimulation, the apparatus including a first reciprocator and a mobile carriage unit, the mobile carriage unit for providing simultaneous application of two or more of the modalities and including a fulcrum adapted and arranged to be in contact with the person's head region generally below the person's occipital condyles, and the first reciprocator adapted and arranged to be in contact with the person's head region for reciprocating the person's head along an arcuate path generally perpendicular to the person's spine when the fulcrum and the first reciprocator are in contact with the person's head region; and
a controller in operative engagement with the modalities for enabling an operator of the pain relieving device to select which one or more of the pain relieving modalities from the group are applied to the person at any given time, the controller causing the pain relieving apparatus to automatically apply the selected modalities to the person.

45. The pain relieving device of claim 44, wherein the controller applies three or more pain relieving modalities simultaneously.

46. The pain relieving device of claim 44, further including a second reciprocator, wherein the second reciprocator reciprocates the fulcrum along a path generally parallel to the person's spine when the fulcrum is in contact with the person's head region.

47. The pain relieving device of claim 44, wherein the fulcrum is operatively engaged with an electrical source to electrically stimulate the person's head region.

48. The pain relieving device of claim 44, wherein the fulcrum is operatively engaged with a heat source to heat the person's head region.

49. A pain relieving device comprising;
a fulcrum adapted to support and contact a person's head region at an area generally below the occipital condyles when the person is in the supine position;
means for applying electric current to the fulcrum to electrically stimulate the area generally below the occipital condyles;
a heater to apply heat to the fulcrum to heat the area generally below the occipital condyles;
a first reciprocator operatively engaged to the fulcrum, the first reciprocator adapted and arranged to reciprocate the fulcrum in a direction generally parallel to the spine of the person to massage the area generally below the occipital condyles; and
a vibrator operatively engaged to the fulcrum, the vibrator adapted and arranged to vibrate the fulcrum to vibrate the area generally below the occipital condyles.

50. The pain relieving device of claim 49, including a second reciprocator operatively engaged to the person's head region, the second reciprocator adapted and arranged to reciprocate the person's head region on the fulcrum along a generally arcuate path in a direction generally perpendicular to the spine of the person to massage the area generally below the occipital condyles.

51. A method for relieving pain comprising the steps of;
supporting and contacting a person's head region on a fulcrum at an area generally below the occipital condyles when the person is in the supine position;
applying electric current to the fulcrum to electrically stimulate the area generally below the occipital condyles;

applying heat to the fulcrum to heat the area generally below the occipital condyles;

reciprocating the fulcrum in a direction generally parallel to the spine of the person to massage the area generally below the occipital condyles;

reciprocating the person's head region on the fulcrum along a generally arcuate path in a direction generally perpendicular to the spine of the person to massage the area generally below the occipital condyles; and vibrating the fulcrum to vibrate the area generally below the occipital condyles.

52. A pain relieving device comprising;

pain relieving apparatus for selectively applying three or more pain relieving modalities to an upper body region of a person, the modalities including acupressure and at least two other modalities selected from the group of vibration, massage, and electric stimulation;

an electrode for applying the heat and electric stimulation modalities;

means for enabling an operator of the pain relieving device to select which three or more of the pain relieving modalities are applied to the person at any given time; and means for causing the pain relieving apparatus to automatically apply the selected modalities to the person.

53. The pain reducing device of claim 52, wherein the selection means is a hand-held controller.

54. The pain reducing device of claim 52, wherein the group of modalities includes traction or heat.

55. the pain relieving device of claim 52, wherein the electrode is a silver-silicone electrode made from a mixture of approximately 70–75% by weight silver coated glass microspheres and silicone rubber.

56. The pain relieving device of claim 52, wherein the electrode applies the vibration modality.

57. A device for relieving pain by applying pain relieving modalities comprising;

a fulcrum for supporting and contacting a person's head region at an area generally below the occipital condyles when the person is in the supine position, the fulcrum including an electrode to electrically stimulate the area generally below the occipital condyles;

means for applying electric current to the electrode;

a heater to apply heat to the electrode to heat the area generally below the occipital condyles;

a massager for reciprocating the fulcrum to massage the area generally below the occipital condyles, and for reciprocating the person's head region on the fulcrum to massage the area generally below the occipital condyles; and a vibrator for vibrating the electrode to vibrate the area generally below the occipital condyles.

58. The pain relieving device of claim 57, wherein the electrode is a silver-silicone electrode made from a mixture of approximately 70–75% by weight silver coated glass microspheres and silicone rubber.

59. A pain relieving device comprising;

a fulcrum adapted to support and contact a person's head region at an area generally below the occipital condyles when the person is in the supine position, the fulcrum including an electrode to electrically stimulate the area generally below the occipital condyles;

means for applying electric current to the electrode;

a heater to apply heat to the electrode to heat the area generally below the occipital condyles;

a first reciprocator operatively engaged to the fulcrum, the first reciprocator adapted and arranged to reciprocate the fulcrum in a direction generally parallel to the spine of the person to massage the area generally below the occipital condyles; and a vibrator operatively engaged to the electrode, the vibrator adapted and arranged to vibrate the electrode to vibrate the area generally below the occipital condyles.

60. The pain relieving device of claim 59, including a second reciprocator operatively engaged to the person's head region, the second reciprocator adapted and arranged to reciprocate the person's head region on the fulcrum along a generally arcuate path in a direction generally perpendicular to the spine of the person to massage the area generally below the occipital condyles.

61. The pain relieving device of claim 59, wherein the electrode is a silver-silicone electrode made from a mixture of approximately 70–75% by weight silver coated glass microspheres and silicone rubber.

62. A method for relieving pain comprising the steps of;

supporting and contacting a person's head region on a fulcrum at an area generally below the occipital condyles when the person is in the supine position, the fulcrum including an electrode to electrically stimulate the area generally below the occipital condyles;

applying electric current to the electrode to electrically stimulate the area generally below the occipital condyles;

applying heat to the electrode to heat the area generally below the occipital condyles;

reciprocating the fulcrum in a direction generally parallel to the spine of the person to massage the area generally below the occipital condyles;

reciprocating the person's head region on the fulcrum along a generally arcuate path in a direction generally perpendicular to the spine of the person to massage the area generally below the occipital condyles; and vibrating the electrode to vibrate the area generally below the occipital condyles.

63. An apparatus for relieving pain comprising;

a carriage for supporting and contacting a person's head region on a fulcrum at an area generally below the occipital condyles when the person is in the supine position, the fulcrum including an electrode to electrically stimulate the area generally below the occipital condyles;

means for applying electric current to the electrode to electrically stimulate the area generally below the occipital condyles; and means for applying heat to the electrode to heat the area generally below the occipital condyles.

64. The apparatus of claim 63, including means for reciprocating the fulcrum in a direction generally parallel to the spine of the person to massage the area generally below the occipital condyles;

means for reciprocating the person's head region on the fulcrum along a generally arcuate path in a direction generally perpendicular to the spine of the person to massage the area generally below the occipital condyles; and means for vibrating the electrode to vibrate the area generally below the occipital condyles.

65. The apparatus of claim 63, wherein the electrode is a silver-silicone electrode made from a mixture of approximately 70–75% by weight silver coated glass microspheres and silicone rubber.

66. A device for relieving pain by applying pain relieving modalities comprising;

at least one electrode, the at least one electrode applying an electric current to electrically stimulate an area generally below the occipital condyles of a person's body;

a heater applying heat to the at least one electrode;

a carriage, the carriage having at least one of the electrodes disposed thereon;

a massager coupled to the carriage, the massager reciprocating the carriage along a path generally parallel to the person's spine to massage the area generally below the occipital condyles; and a vibrator coupled to the carriage, the vibrator vibrating the area generally below the occipital condyles.

67. The device according to claim 66, wherein the at least one electrode is taken from the group consisting of an occipital electrode, a frontal electrode and a shoulder electrode.

68. A pain relieving device comprising:

a movable carriage;

a first occipital electrode mounted on the carriage, the first occipital electrode adapted to support a person's head when the person is lying in the supine position, and adapted to be in contact with the general area of the person's head below the occipital condyles;

a strap for encircling the forehead of the person;

a massage apparatus to reciprocate the strap so that the person's head reciprocates along an arcuate path in a direction generally perpendicular to the person's spine, and to reciprocate the carriage in a direction generally parallel to the patient's spine;

an electrical stimulator, the electrical stimulator applying an electric current to the first occipital electrode to provide electric stimulation; and a heater, the heater applying heat to the first occipital electrode to provide heat stimulation to the general area of the person's head below the occipital condyles.

69. The pain relieving device of claim 68, further including a vibrator to vibrate the general area of the person's head below the occipital condyles.

70. The pain relieving device of claim 68, further including a first shoulder electrode and a second shoulder electrode adapted to be in contact with the region generally above the person's shoulder blades and wherein the strap includes a first frontal electrode and a second frontal electrode adapted to generally be in contact with the frontal region of a person's forehead.

71. The pain relieving device of claim 70, wherein the electrical stimulator further applies the electric current between the first occipital electrode and the second frontal electrode.

72. The pain relieving device of claim 70, wherein the electrical stimulator applies the electric current between the first occipital electrode and the second shoulder electrode.

73. The pain relieving device of claim 70, wherein the electrical stimulator applies the electric current between the first occipital electrode and the second frontal and the second shoulder electrodes.

74. The pain relieving device of claim 70, further including a second occipital electrode mounted on the carriage, the second occipital electrode adapted to support a person's head when the person is lying in the supine position, and adapted to be in contact with the general area of the person's head below the occipital condyles, wherein the electrical stimulator applies the electric current between the first and second occipital electrodes and the first and second shoulder electrodes.

75. The pain relieving device of claim 70, further comprising a second occipital electrode, a third occipital electrode and a fourth occipital electrode mounted on the carriage, the second occipital electrode, the third occipital electrode and the fourth occipital electrode adapted to support a person's head when the person is lying in the supine position, and adapted to be in contact with the general area of the person's head below the occipital condyles, wherein the electrical stimulator applies the electric current between the first frontal electrode and the first shoulder electrode, the second frontal electrode and the second shoulder electrode, the first occipital electrode and the fourth occipital electrode, and the third occipital electrode and the second occipital electrode.

76. The pain relieving device of claim 70, further comprising a second occipital electrode, a third occipital electrode and a fourth occipital electrode mounted on the carriage, the second occipital electrode, the third occipital electrode and the fourth occipital electrode adapted to support a person's head when the person is lying in the supine position, and adapted to be in contact with the general area of the person's head below the occipital condyles, wherein the electrical stimulator applies the electric current between the first frontal electrode and the second shoulder electrode, the second frontal electrode and the first shoulder electrode, the first occipital electrode and the fourth occipital electrode, and the third occipital electrode and the second occipital electrode.

77. The pain relieving device of claim 68, wherein the electrical stimulator applies the electric current between the general areas of the person's upper body selected from the group consisting of the area below the occipital condyles, the frontal region and the area above the shoulder blades to provide electric stimulation.

78. The pain relieving device of claim 68, wherein the massage apparatus includes a motor operatively engaged to the strap and a crank driven by the motor.

79. A pain relieving device comprising;

a fulcrum adapted to support and contact a person's head region at an area generally below the occipital condyles when the person is in the supine position;

an electric stimulator, the electric stimulator applying electric current to the fulcrum to electrically stimulate the area generally below the occipital condyles;

a heater, the heater applying heat to the fulcrum to heat the area generally below the occipital condyles;

a first reciprocator operatively engaged to the fulcrum, the first reciprocator adapted and arranged to reciprocate the fulcrum in a direction generally parallel to the spine of the person to massage the area generally below the occipital condyles; and a vibrator operatively engaged to the fulcrum, the vibrator adapted and arranged to vibrate the fulcrum to vibrate the area generally below the occipital condyles.

80. The pain relieving device of claim 79, further including a second reciprocator operatively engaged to the patient's head region, the second reciprocator adapted and arranged to reciprocate the patient's head on the fulcrum along a generally arcuate path in a direction generally perpendicular to the spine of the patient to massage the area generally below the occipital condyles.

81. An apparatus for relieving pain comprising;
a carriage for supporting and contacting a person's head region on a fulcrum at an area generally below the occipital condyles when the person is in the supine position, the fulcrum including an electrode to electrically stimulate the area generally below the occipital condyles;
an electric stimulator, the electric stimulator applying electric current to the electrode to electrically stimulate the area generally below the occipital condyles; and
a heater, the heater applying heat to the electrode to heat the area generally below the occipital condyles.

82. A pain relieving device comprising:
a fulcrum supporting and contacting a person's head region at an area generally below the occipital condyles when the person is in the supine position;
an electric stimulator, the electric stimulator applying electric current to the fulcrum to electrically stimulate the area generally below the occipital condyles;
a first reciprocator, the reciprocator reciprocating the fulcrum to massage the area generally below the occipital condyles; and
a vibrator, the vibrator vibrating the fulcrum to vibrate the area generally below the occipital condyles.

83. The pain relieving device of claim 82, wherein the device includes a second reciprocator, the second reciprocator adapted and arranged to reciprocate the patient's head region the fulcrum along a generally arcuate path in a direction generally perpendicular to the spine of the patient to massage the area generally below the occipital condyles.

* * * * *